US009389166B2

(12) United States Patent
Wolf et al.

(10) Patent No.: US 9,389,166 B2
(45) Date of Patent: Jul. 12, 2016

(54) ENHANCED HIGH-SPEED LOGARITHMIC PHOTO-DETECTOR FOR SPOT SCANNING SYSTEM

(71) Applicant: KLA-Tencor Corporation, Milpitas, CA (US)

(72) Inventors: Ralph C. Wolf, Palo Alto, CA (US); Grace H. Chen, Los Gatos, CA (US); Kai Cao, Fremont, CA (US); Jamie M. Sullivan, Sunnyvale, CA (US); Paul J. Donders, Fremont, CA (US); Derek C. Mackay, Menlo Park, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 429 days.

(21) Appl. No.: 13/675,687

(22) Filed: Nov. 13, 2012

(65) Prior Publication Data
US 2013/0169957 A1    Jul. 4, 2013

Related U.S. Application Data

(60) Provisional application No. 61/576,702, filed on Dec. 16, 2011, provisional application No. 61/700,527, filed on Sep. 13, 2012.

(51) Int. Cl.
G01N 21/00    (2006.01)
G01N 21/88    (2006.01)
G01N 21/95    (2006.01)
G01N 21/956   (2006.01)
G01B 11/24    (2006.01)

(52) U.S. Cl.
CPC ............... *G01N 21/00* (2013.01); *G01B 11/24* (2013.01); *G01N 21/8851* (2013.01); *G01N 21/9501* (2013.01); *G01N 21/956* (2013.01)

(58) Field of Classification Search
CPC ..... H04N 9/3185; H04N 9/3197; G06T 1/005
USPC ...................... 356/237.1–237.6, 239.3–239.5
See application file for complete search history.

(56) References Cited

U.S. PATENT DOCUMENTS 6,002,122 A    12/1999    Wolf
6,177,665 B1    1/2001    Wolf
(Continued)

FOREIGN PATENT DOCUMENTS

JP    2011-179947 A    9/2011
KR    10-0758460 B1    9/2007

OTHER PUBLICATIONS

"International Application Serial No. PCT/US2012/069906, Search Report and Written Opinion mailed Apr. 25, 2013", 12 pgs.

*Primary Examiner* — Kara E Geisel
*Assistant Examiner* — Iyabo S Alli
(74) *Attorney, Agent, or Firm* — Kwan & Olynick LLP

(57) ABSTRACT

Disclosed are apparatus and methods for inspecting or measuring a specimen. An incident beam is directed across a plurality of consecutive scan portions of a specimen so that an output beam profile from each scan portion is consecutively collected by a photomultiplier tube (PMT), and the scan portions include at least one or more first scan portions and a next scan portion that is scanned after the one or more first scan portions. After or while the incident beam is directed to the one or more first scan portions of the specimen, an output signal for each first scan portion is obtained based on the output beam profile that is collected by the PMT for each first scan portion. An expected output beam profile for the next scan portion is determined based on the output signal that is obtained for each one or more first scan portions. As the incident beam is directed towards the next scan portion, a gain input to the PMT for the next scan portion is set based on the expected output beam profile so that the gain for such next scan portion results in a measured signal at the PMT that is within a predefined specification of the PMT or other hardware components that receive a measured signal from the PMT.

22 Claims, 13 Drawing Sheets

(56) References Cited

U.S. PATENT DOCUMENTS

| | | |
|---|---|---|
| 6,252,412 B1 | 6/2001 | Talbot et al. |
| 6,833,913 B1 * | 12/2004 | Wolf ............... G01N 21/47 356/237.2 |
| 6,909,561 B2 * | 6/2005 | Buchholz ............... 359/896 |
| 2002/0145732 A1 | 10/2002 | Vaez-Iravani et al. |
| 2002/0161534 A1 | 10/2002 | Adler et al. |

* cited by examiner

ENHANCED HIGH-SPEED LOGARITHMIC PHOTO-DETECTOR FOR SPOT SCANNING SYSTEM

CROSS-REFERENCE TO RELATED APPLICATIONS

This application claims the benefit of prior applications U.S. Provisional Application No. 61/576,702, filed 16 Dec. 2011 by Ralph C. Wolf et al. and Application No. 61/700,527, filed 13 Sep. 2012 by Ralph C. Wolf et al., which applications are herein incorporated by reference in their entirety for all purposes.

TECHNICAL FIELD OF THE INVENTION

The present invention relates generally to inspection and metrology systems. More specifically, it relates to light collection mechanisms for inspecting and measuring semiconductor wafers and other types of patterned samples.

BACKGROUND

Some conventional optical inspection tools locate defects on patterned wafers by scanning the surface of the wafer with a tightly focused laser spot and measuring the amount of light scattered by the illuminated spot on the wafer. Dissimilarities in the scattering intensity between similar locations in adjacent dies are recorded as potential defect sites.

The dynamic range of this optical scattering is typically substantial. Changes in scattering intensity of more than a million to one within a single die are not uncommon. This high dynamic range is intrinsic to the optical configuration of the instrument and the scattering properties of the wafers and defects of interest.

Optical sensing is the process of converting optical signals (photons) into electrical signals (electrons). When the optical signals are dim, and frequencies are high, photomultiplier tubes are typically used. A photomultiplier tube generally includes a photocathode, one or more dynodes, and an anode. Individual photons striking the cathode have a particular probability (e.g., 25%) of dislodging an electron. These photoelectrons are then accelerated towards the first dynode by an electric field. When the electrons strike the dynode they dislodge additional electrons, thus amplifying the signal. These secondary electrons then cascade towards the next dynode where they are again amplified. At the end of the dynode chain, the electrons are collected by the anode which carries them outside of the photomultiplier tube. At this point, the signal is large enough to be easily measured using conventional electronics, such as a transimpedance amplifier, followed by an analog-to-digital converter.

The gain at each dynode is a function of the energy of the incoming electron, which is proportional to the electric potential between that dynode and the previous stage. The total gain of the tube is the product of the gains from all the dynodes. There are continued efforts to improve photomultiplier tube gain control.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting or measuring a specimen is disclosed. An incident beam is directed across a plurality of consecutive scan portions of a specimen so that an output beam profile from each scan portion is consecutively collected by a photomultiplier tube (PMT), and the scan portions include at least one or more first scan portions and a next scan portion that is scanned after the one or more first scan portions. After or while the incident beam is directed to the one or more first scan portions of the specimen, an output signal for each first scan portion is obtained based on the output beam profile that is collected by the PMT for each first scan portion. An expected output beam profile for the next scan portion is determined based on the output signal that is obtained for each one or more first scan portions. As the incident beam is directed towards the next scan portion, a gain input to the PMT for the next scan portion is set based on the expected output beam profile so that the gain for such next scan portion results in a measured signal at the PMT that is within a predefined specification of the PMT or other hardware components that receive a measured signal from the PMT.

In a specific implementation, each one or more first scanned portions comprises a first die and the next scan portion comprises a second die that differs from each one or more first die. In another implementation, each one or more first scanned portions comprises one or more first scan lines and the next scan portion comprises a second scan line that is adjacent to the one or more first scan lines. In a further aspect, the output signal for the one or more first scan portions is also analyzed to detect defects in such one or more first scan portions. In another further aspect, the scan portions, towards which the incident beam is directed, further include a second next scan portion that is adjacent to the first next scan portion, and the method further comprises (i) after or while the incident beam is directed to the first next scan portion of the specimen, obtaining an output signal for the first next scan portion based on the output beam profile that is collected by the PMT for such first next scan portion; (ii) determining an expected output beam profile for the second next scan portion based on the output signal that is obtained for the first next scan portion; and (iii) as the incident beam is directed towards the second next scan portion, setting a gain input to the PMT for the second next scan portion based on the expected output beam profile for the second next scan portion so that the gain for such second next scan portion results in a measured signal at the PMT that is within a predefined specification of the PMT. In a further aspect, the gain input to the PMT for the first and second next scan portion are set so as to be limited to a particular frequency range.

In another specific implementation, the expected output beam profile for the next scan portion is predicted to be substantially equal to the output beam profile for a most recently scanned one of the first scan portions or an average of the output beam profiles for the one or more first scan portions. In another example, the one or more first scan portions comprise a plurality of first scan portions and the expected output beam profile for the next scan portion is predicted to have a rate of gain increase or decrease from the immediately previously scanned one of the first scan portions that is substantially equal to a rate of gain increase or decrease for first scan portions. In yet another example, the one or more first scan portions comprise a plurality of first scan portions and the expected output beam profile is predicted to have a rate of gain increase or decrease from the immediately previously scanned one of the first scan portions that is that is proportional to a rate of gain increase or decrease for the first scan portions.

In one embodiment, the gain is further set so that such gain is aligned to coincide with scanning of the next scan portion and kept within a predetermined range of values so as to minimize artifacts in an image generated from a measured signal output by the PMT for the next scan portion. In another aspect, the gain is input to the PMT for the next scan portion by inputting two gain signals to the PMT that are 180 degrees out of phase and substantially identical in magnitude, wherein one of the two gain signals is received by a first half of dynodes of the PMT and another one of the two gain signals is received by another half of dynodes of the PMT.

In an alternative embodiment, the invention pertains to a system for inspecting or measuring a specimen. This system comprises a photomultiplier tube (PMT) for sensing light emanating from a specimen in response to an incident beam directed towards such specimen and a beam generator for directing the incident beam across a plurality of consecutive scan portions of the specimen so that an output beam profile from each scan portion is consecutively collected by the PMT. The scan portions include one or more first scan portions and a next scan portion that is scanned after the one or more first scan portions. The system further comprises a detection module including the PMT and one or more detection components for generating a response signal for each scan portion as the incident beam is scanned over such scan portions and a gain prediction module for receiving the response signal for each scan portion from the detection module and setting a gain of the PMT based on such response signal. The gain for each scan portion of the specimen is set based on predicting the light that is expected to emanate from such scan portion based on the response signal generated from one or more previous scan portions of the specimen that were most recently scanned by the incident beam.

In a specific aspect, the gain input for each scan portion is set so that such gain results in a measured signal at the PMT that is within a predefined specification of the PMT or other hardware components of the detection module or gain prediction module that receive a measured signal from the PMT. In a further aspect, the system includes a processor for analyzing the response signal for each scan portion to detect defects in such scan portion. In further embodiments, the system implements one or more of the above-described method operations.

In another embodiment, the invention pertains to at least one computer readable storage medium having computer program instructions stored thereon that are arranged to cause an inspection or metrology tool to perform one or more of the above-described method operations.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Certain embodiments of a high-speed logarithmic photo-detector system may be utilized in any suitable optical inspection or metrology system. In one general example, the system is configured to quickly detect a relatively wide dynamic range of intensity values from a beam (e.g., scattered light, reflected light, or secondary electrons) originating from a sample, such as a semiconductor wafer, without significant image artifacts. The detected output signals may then be analyzed to determine whether defects are present on the sample. For example, the intensity values from a target die are compared to the intensity values from a corresponding portion of a reference die, where a significant intensity difference may be defined as a defect. These inspection systems may implement any suitable inspection technology, along with the novel detector mechanisms described further below. By way of examples, brightfield and/or darkfield optical inspection mechanisms may be utilized. The mechanisms of the present invention may also be implemented within a scanning electron microscopy system.

Figure 1:
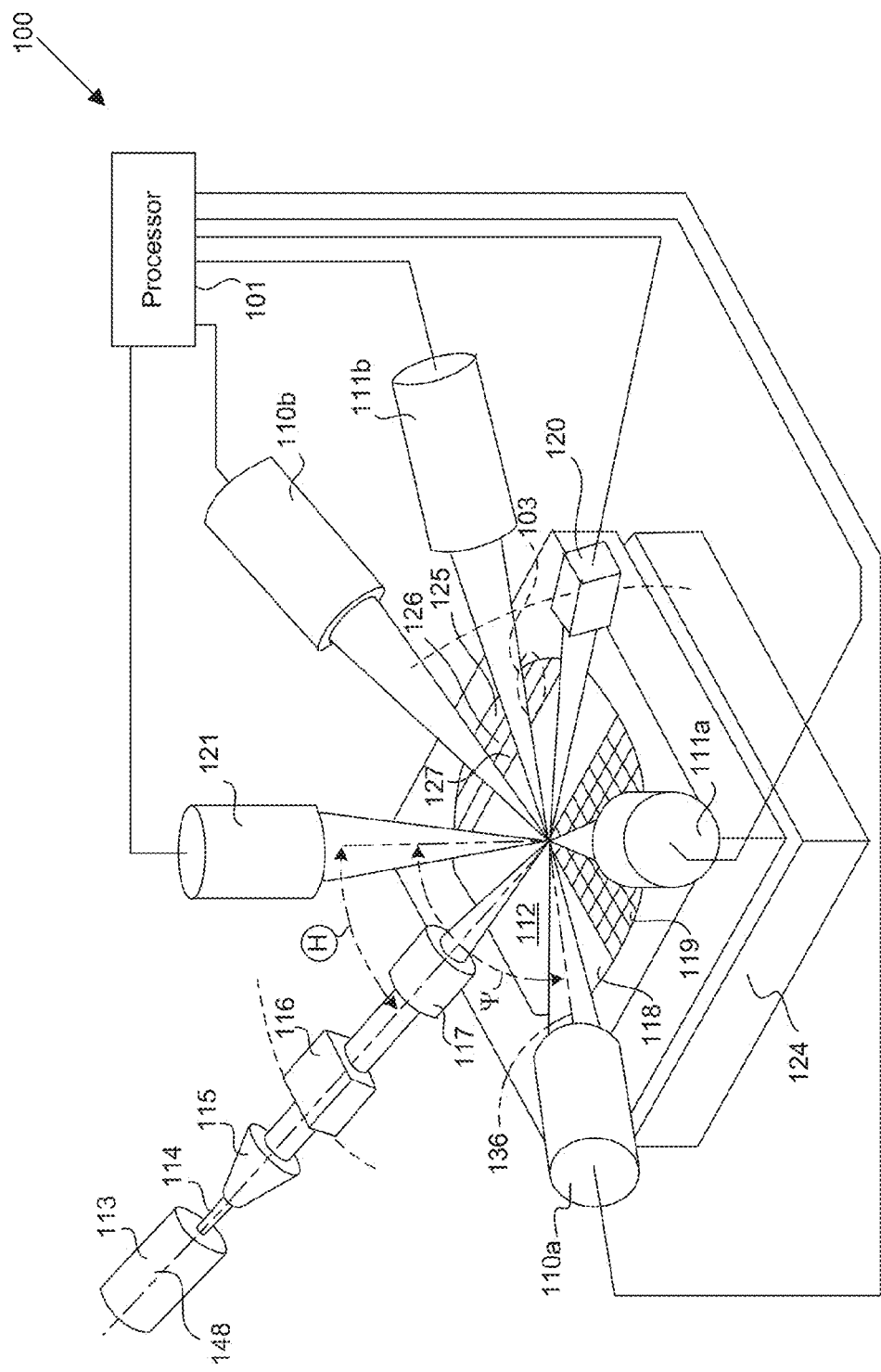
FIG. 1 is a diagrammatic representation of an optical inspection system in accordance with one embodiment of the present invention.

FIG. 1 is a diagrammatic representation of an optical system 100 in accordance with one embodiment of the present invention. The optical system includes any suitable number of detectors or collection channels for detecting light emitted from a sample, such as a semiconductor surface. The detectors or collection channels may be arranged in any suitable positions, which depend on the particular requirements of the inspection or metrology application. The illustrated embodiment uses two groups of two collector channels, 110a-b and 111a-b, disposed symmetrically about the wafer surface 112 so that each collector channel within a pair is located at the same azimuthal angle on opposite sides of the scan line. These azimuthal collector channels detect scattered light.

The output from the collector channels may then be sent to processor 101 for data analysis and/or image generation. The data from the channels can be compared by performing various algorithms and logical operations, e.g., OR, AND and XOR.

The optical system also includes a beam generator (e.g., components 113, 115, 116, and 117) for generating an incident beam and directing it towards a sample. As shown in FIG. 1, a light source 113, typically a laser, emits a beam 114. Beam 114 is directed towards a pre-deflector optics 115, which may include of a half wave-plate, a spatial filter and several cylindrical lenses, in order to produce an elliptical beam with a desired polarization that is compatible with the scanner 116. The pre-deflector optics 115 may be configured to expand the beam 114 to obtain the appropriate numerical aperture. The post-deflector optics 117 may include several cylindrical lenses and an air slit. Finally, the beam 114 may be brought into focus on the wafer surface 112 and scanned in the plane of the wafer surface 112. The type of deflector employed in the apparatus is application dependent and may include a polygonal mirror or galvanometer. In one embodiment, deflector 116 is an Acousto-optic Deflector. The wafer surface 112 may be smooth 118 or patterned 119. In addition to the collector channels 110a-b and 111a-b, described above, detector channels may be provided which include a reflectivity/autoposition channel 120, and a normal collector channel 121.

The wavelength of the beam 114 depends on the particular requirements of the application. For example, the beam 114 can have a wavelength of about 488 nm and be produced by any suitable light source, such as an Argon ion laser. The optical axis 148 of the beam 114 may be directed onto the wafer surface 112 at angle θ. This angle θ can be any suitable angle, such as in the range of 55-85 degrees with respect to the normal to the wafer surface 112, depending on the application.

The scanning mechanism may include the deflector 116 and the translation stage 124, upon which the wafer rests. The position of the wafer on the stage 124 is maintained in any convenient manner, e.g., via vacuum suction. The stage 124 may move to partition the surface 112 into striped regions, shown as 125, 126 and 127 with the deflector 116 moving the beam across the width of the striped regions.

Figure 3:
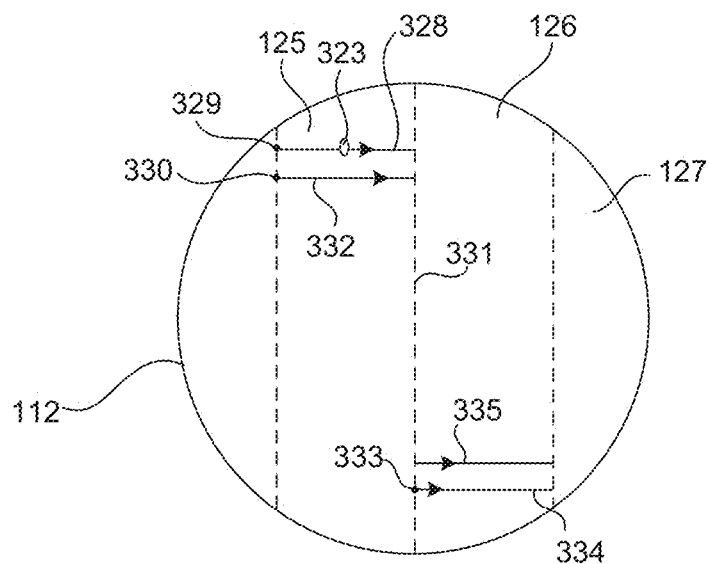
FIG. 3 is a detailed view showing the scan path of a spot on a wafer surface in accordance with one embodiment of the present invention.

Referring to FIG. 3, the grazing angle of the beam 114 produces an elliptical spot 323 on the wafer surface 112, having a major axis perpendicular to the scan line in certain implementations. The deflector 116 may operate to scan the spot 323 across a short scan line equal in length to the width of striped region 125 to produce specularly reflected and scattered light. The spot 323 may be scanned in the direction indicated, as the stage 124 moves the wafer perpendicular to the scan line. This scanning results in the spot 323 moving within the striped region 125, as shown in FIG. 3. In the illustrated embodiment, the spot 323 scans in the direction as indicated by scan path 328. Scan path 328 has an effective start location at 329 and the spot 323 moves to the right therefrom until it reaches the border 331 of striped region 125. Upon reaching border 331, the spot 323 moves relative to the stage 124 perpendicular to the scan direction and the spot is then positioned at a new start position 330 and moves parallel to scan line 328, along scan line 332. The deflector 116 continues to scan the spot 323 in this fashion along the entire length of striped region 125. Upon completion of the scan of striped region 125, the stage 124 moves relative to the wafer to permit the scanning of the adjacent striped region 126. The effective start location 333 is positioned so that the stage 124 shall move perpendicular to each scan line in a direction opposite to that when scanning striped region 125, thereby forming a serpentine scan. This is demonstrated by scan paths 334 and 335. Moving the stage 124 to scan adjacent striped regions in opposite directions substantially reduces the amount of mechanical movement of the stage while increasing the number of wafers scanned per hour.

Figure 2:
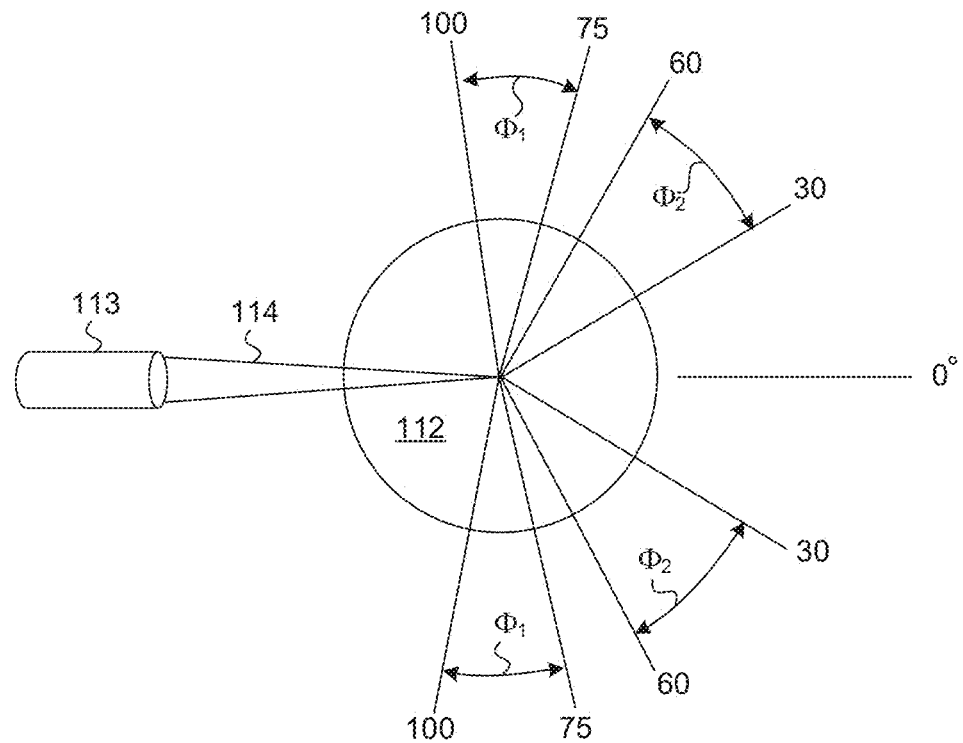
FIG. 2 is a top view of the illumination and collection channels of FIG. 1 in accordance with one embodiment of the present invention.

Referring to FIGS. 1 and 2, light scattered from the wafer surface 112 may be detected by one or more detectors, such as collector channels 110a-b and 111a-b. The collector channels may be arranged to collect light over a fixed solid angle, dependent upon, inter alia, the elevational and azimuthal angle of the channel. The optical axis of each collection channel may be positioned at an angle of elevation ψ in the range of 0 to 90 degrees with respect to the normal to the surface 112. As discussed above, collector channels 110a and 110b can be symmetrically positioned at the same azimuthal angle with respect to beam 114, on opposite sides of the scan line. Collector channels 110a and 110b can be positioned, with respect to the beam 114, at an azimuthal angle $\psi_1$ in the range of about 75 to about 105 degrees to collect laterally scattered light. Laterally scattered light may be defined as light scattered at azimuthal angles in the range of about 75 to about 105 degrees, with respect to beam 114. Similar to collector channels 110a and 110b, channels 111a and 111b may be positioned on opposite sides of the scan line at the same azimuthal angle; however, the azimuthal angles $\psi_2$ of channels 111a and 111b can be in the range of 30 to 60 degrees, to collect forwardly scattered light. Forwardly scattered light can be defined as light scattered at azimuthal angles in the range of 30 to 60 degrees. Of course, the number and location of the collector channels and/or their collection solid angle may be changed in various alternative embodiments without departing from the scope of the invention.

The bright field reflectivity/autoposition channel 120, may be positioned in front of the beam 114 to collect specularly reflected light. The bright field signal derived from this channel carries information concerning the pattern, local variations in reflectivity and height. This channel is sensitive to detecting various defects on a surface. For example, the bright field signal is sensitive to representing film thickness variations, discoloration, stains and local changes in dielectric constant. The bright field signal can also be used to produce an error height signal, corresponding to a variation in wafer height, which is fed to a z-stage to adjust the height accordingly. Finally, the bright field signal can be used to construct a reflectivity map of the surface. This channel can be arranged as an unfolded Type I confocal microscope operating in reflection mode so that the illuminating beam and reflected beams are not collinear. Alternatively, the illuminating and reflected beams are collinear.

The normal collector channel 121 can be arranged to collect light over a fixed solid angle over a region which is approximately perpendicular to the plane of the wafer. Other than the collection solid angle, the normal collector implementation may be similar to the other collector channels 110*ab* and 111*ab*. The normal collector may be used to collect scattered light from the intentional patterns on the wafer, as well as to detect defects which scatter light in an upwards direction. Signals collected from the intentional patterns can be used to facilitate the alignment and registration of the wafer pattern to the coordinate system of the mechanical stage in the instrument.

One or more of the collector channels include high-speed logarithmic photo-detector mechanism for increasing the dynamic range of detected output signals. These photo-detector mechanisms may be provided within one or more of collector channels 110*ab*, 111*ab* and 121. In general terms, a photo-detector collector includes a light sensor, such as a photomultiplier tube (PMT) for generating a signal from detected photons and an analog to digital converter (ADC) for converting the light signal to a digital light signal. Of course, other suitable mechanism may be used for sensing light and converting an analog signal into a digital signal.

The photo-detector collector also includes mechanisms for automatically adjusting the gain of the PMT. Several embodiments for automatically adjusting gain of a PMT are further described in U.S. Pat. No. 6,833,913, issued 21 Dec. 2004, and U.S. Pat. No. 6,177,665, issued 23 Jan. 2001, which patents are incorporated herein by reference in their entirety. In one described approach, the collector includes a high-speed feedback or control loop mechanism to continuously modulate the gain of the PMT in response to the current detected signal strength of the anode. When the anode output is high, the control loop lowers PMT gain so that high intensity optical signal would not saturate the PMT. Conversely, when the anode output is low, the control loop raises the PMT gain to increase the sensitivity of low intensity optical signal. The gain information is captured independently from the anode current, and the two data streams are recombined digitally to construct a single optical information data stream.

Although a basic gain adjustment technique can allow the inspection system to receive optical signals across a very large intensity range, such an approach may have an inherent time delay in the analog gain control loop. For signals which are changing quickly, the propagation delay of the control loop leads to a reactive system. In the extreme case of a point defect on a bare wafer, this type of system only reacts after the brightest part of the signal has already passed. The system then lowers the gain in a region that should be inspected at a high gain. In a control loop approach, the PMT gain for a particular pixel is determined from the amplitude of anode current of the previous pixel that was last scanned by the system. Since the gain is reacting to the immediate past in the same scan line, the gain change always lags behind the actual detected signal.

Figure 6A:
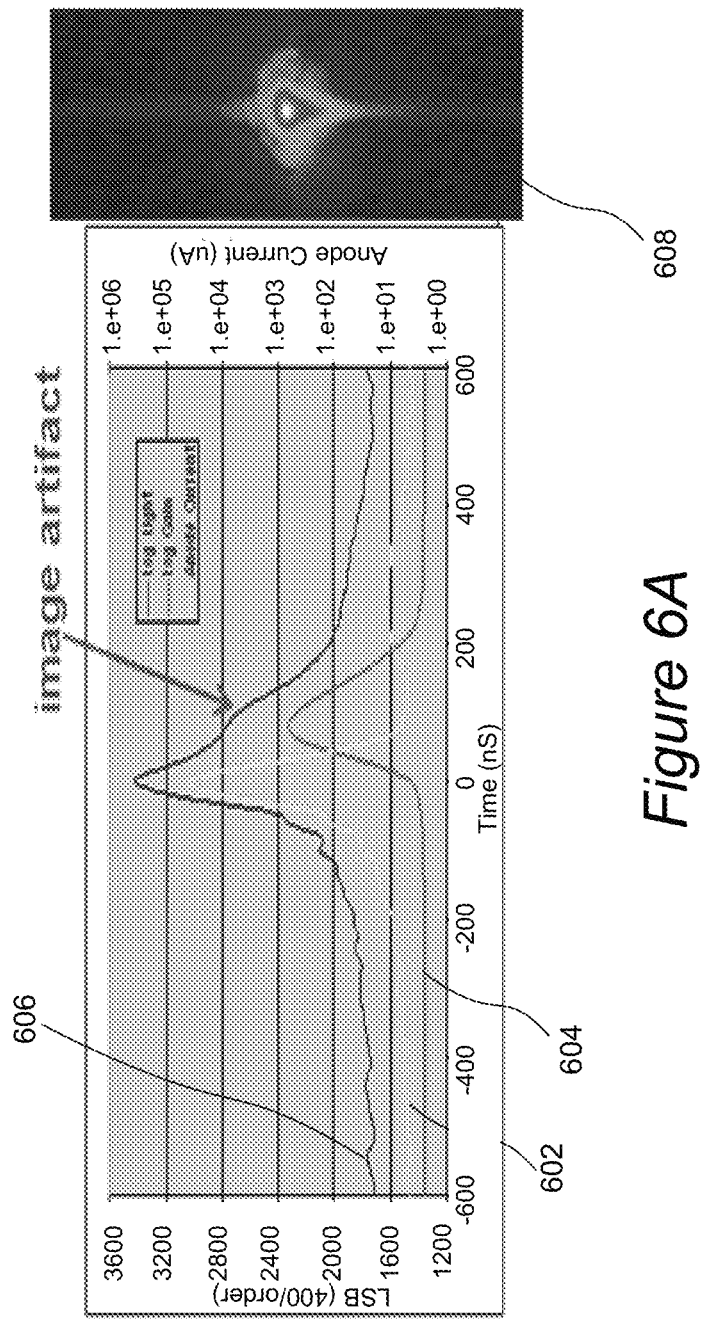
FIG. 6A shows results produced by a particular PMT gain adjustment solution, in which the optical bandwidth exceeds the detection system's capability.

When the optical signal bandwidth exceeds the system's capability, large anode current excursions can lead to artifacts in the reconstructed signal. FIG. 6A shows an example in which the optical bandwidth exceeds the detection system's capability. In this example, the anode current output 602, gain signal 604, and the reconstructed image signal 606 (of the specimen) are graphed with respect to time (nS). It is noted that an inverse gain is actually plotted so that a higher value corresponds to a higher optical signal. It is clear that the gain signal 604 is delayed from the anode current 602. The gain 604 is still falling (illustrated as an inverted rising signal) after the peak has passed and the anode current 602 starts to fall. This delay results in slew rates in the anode current 602 that exceed the capabilities of the log amplifier, causing the reconstructed signal 606 to exhibit an asymmetric tail in the trailing side (labeled "image artifact" in the plot). An image of the artifact, which is "tear drop like", is also shown as 2D image 608 in FIG. 6A. Also, the gain remains at near maximum values (shown as an inverted minimum value in inverted gain signal 604) when the brightest part of the optical signal is measured, resulting in very large anode currents of up to 40 mA, which far exceeds the typical maximum average anode current rating for a PMT having a 0.1 mA specification.

Certain embodiments of the present invention substantially eliminate this tear drop artifact by using techniques to predict the required gain for each scan line based on measurements from one or more previous scan lines. It has been observed that the spatial resolution of the image is limited by the point spread function (PSF) of the laser spot. For example, one type of inspection tool may have a laser spot that covers 3½ scan lines at a time, and each line is not immediately exposed to the full power of the spot. For a bright part of the sample, the light detected from the sample for each scanned line slowly increases as the spot moves towards the bright portion of the sample. That is, one scan line will not be fully dark and then the next adjacent line will become fully bright. Additionally, it has also been observed that the sample rate, in terms of number of samples per $1/e^2$ diameter, is the same in X and Y directions. These observations mean that the prior pixels in the X direction are just as good as predicting the approximate intensity of an unmeasured pixel as the prior pixels in the y direction. By constructing a gain control waveform for a particular scan line based on information gathered from prior scan lines, the time lag can be substantially eliminated so that the minimum of the gain coincides with the maximum of the anode current.

Certain embodiments of the present invention include a digital implementation to store and analyze previous scan lines and then send a gain control waveform to the detectors (e.g., PMT) via a high speed digital to analog converter (DAC), for example. Two general implementations are described herein: a "closed loop approach and an "open loop approach. These two approaches differ in their complexity and the time scales over which the prior scan information is retained.

The closed loop approach generally makes no assumptions about the repeatability of the optical signal from die to die or wafer to wafer. This approach uses only information from the most recent prior scan lines to predict the brightness of the next line. Specifically, the previous scan lines may be used to anticipate an intensity range of data to come (e.g., data in the next scan line). This prediction is then used to construct a "best" compromise gain control waveform to keep the anode current near the middle of the receiving log amplifier's operating range.

In an alternative "open loop" solution, the brightness of a die is obtained during a recipe learn phase. A gain waveform is then determined for the entire die to keep the anode current near the middle of the receiving log amplifier's operating range. This same gain waveform or image can then be used to inspect every die. As a result, substantially no propagation delay of gain takes place, and the "tear drop artifact" is substantially eliminated from the measured results. In one implementation, the brightness of a "recipe" die is determined based on design data upon which fabrication and measurement effects are modeled to simulate die brightness. In general, die brightness for a particular die is determined from pre-existing knowledge about the die structure (for example, information from the entity that designed the die). Alternatively, the die is initially scanned at minimum gain. In this alternative process, the die areas that still have low signal are then scanned again at a slightly higher gain. The scanning is repeated on die areas that continue to have a low signal until the entire die has been scanned. This process may be slow, but such setup process would only be done once during recipe setup.

Figure 6B:
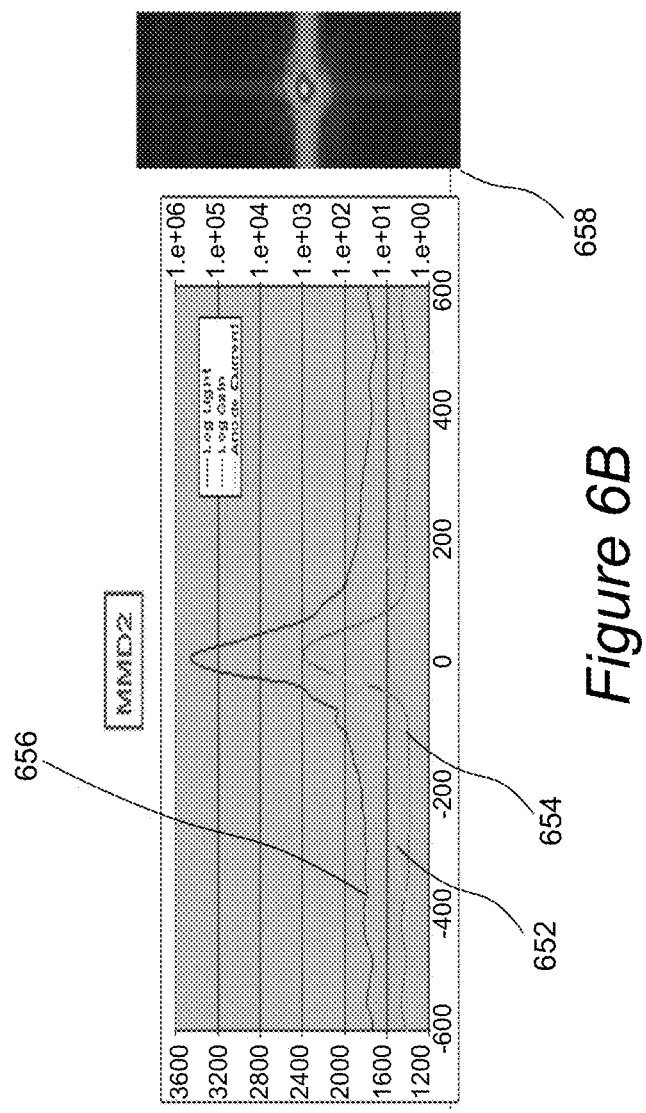
FIG. 6B shows results produced by an "opened loop" solution, in which PMT gain is determined from prior knowledge of wafer structure in accordance with a specific implementation of the present invention.

Certain embodiments of these two solutions include storing data to set the gain (either data from previous lines or wafer dies). To set the gain of PMT, the computed gain value may then be played back, for example, via a DAC (digital analog converter) to the PMT via a control loop with substantially no propagation delay. FIG. 6B shows results produced by an "open loop" solution, in which PMT gain is determined from prior knowledge of wafer structure in accordance with a specific implementation of the present invention. FIG. 6B includes a graph of the anode current 652, inverted gain signal 654, and the reconstructed signal 656 obtained from an "open loop" embodiment. It is clear from the plot that there is substantially no propagation gain delay and the "tear drop" artifact is eliminated as shown in image 658.

Figure 4:
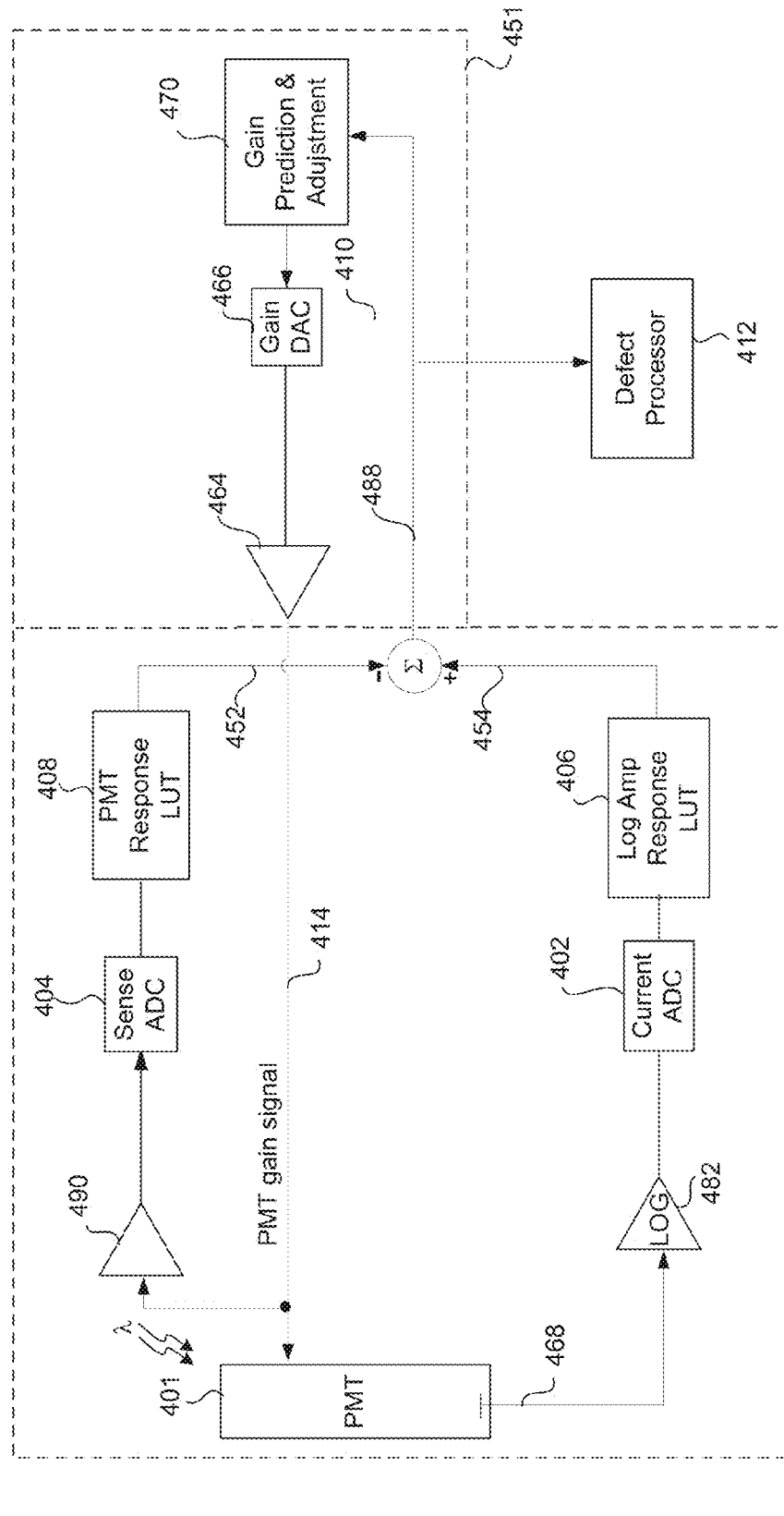
FIG. 4 is a schematic diagram illustrating a high-speed logarithmic photo-detector system according to one embodiment of the present invention

Referring back to a closed loop approach, FIG. 4 is a schematic diagram illustrating a high-speed logarithmic photo-detector system 400 according to one embodiment of the present invention. As shown, the system 200 includes a detection block 450, a gain adjustment block 451, and a defect processor block 412. Any suitable type and number of devices may be utilized to implement the blocks of such system 400, and these blocks may be integrated together on a single device or on a plurality of devices. Example mechanisms are further described below.

The detection block 450 generally senses light emanating from the sample and generates a response signal based on such sensed light. The detection block 450 also senses gain that is input to a sensor by the gain adjustment block 451 and generates a gain signal based on such sensed gain. The detection block 450 is also configured to output a combined response and gain signal to gain adjustment block 451 and defect processor block 412.

The gain adjustment module 451 generally receives the combined gain and response signal, stores such combined signal for one or more scanned lines, and then predicts the gain for a particular next line of the sample based on the stored signal. This gain prediction is then used to adjust the gain to the sensor for the particular line. The gain is received by amplifier 464, which amplifies and output the gain to sensor 401 of the detection module 450. The defect processor 412 generally analyzes the detected signal to determine whether there are defects on the sample.

The detection block 450 may be implemented in any suitable manner for generating a signal that corresponds to both light collected from the sample and the gain 414 that is applied to the sensor or PMT. As shown, detection block 450 includes a sensor in the form of photomultiplier tube (PMT) 401 that receives a PMT gain signal 414 from the control-voltage amplifier 464 of gain adjustment module 451. The PMT 401 converts the light impinging thereon into a measured signal 468, e.g., a current value that is proportional to the light intensity. This measured signal 468 may be sent to logarithmic amplifier 482. Suitable PMT's include a circular cage type PMT, metal-channel photomultiplier, etc.

The logarithmic amplifier 482 can be arranged to produce a signal which is the log of the anode current of PMT 401. Any suitable base value may be utilized by the logarithmic amplifier 482. In one implementation, the logarithmic amplifier 482 is a four-decade log amplifier (such as a model 382 logarithmic amplifier available from Analog Modules, Inc. of Longwood, Fla.).

The detection block 450 may also include a linear amplifier 490 for receiving the gain signal 414 generated by the gain adjustment block 451 and feeding such gain signal back to the gain adjustment block 451 via a sense ADC 404 and PMT Response look up table (LUT) 408.

In general, the outputs of linear amplifier 490 and logarithmic amplifier 482 may be digitized and transformed into ideal logarithmic representations of the detected signal and gain, e.g., to account for the actual gain characteristics of the PMT 401 as it differs from typical response curve or because of errors in logarithmic amplifier 482 or because of current dependent errors originating elsewhere, such as in the PMT itself. In the illustrated embodiment, the outputs of linear amplifier 490 and logarithmic amplifier 482 are separately digitized by sense ADC 404 and current ADC 402, respectively.

The outputs of sense ADC 404 and current ADC 406 may be used to interrogate programmable PMT response LUT 408 and log amp response LUT 406, respectively. LUT 408 and 406 may each be used to implement completely general calibrations which convert the outputs of amplifiers 490 and 482 into ideal logarithmic representations of the gain 452 and anode current 454, having a common pre-determined base.

LUT 406 and 408 may be experimentally determined for individual particular embodiments of the invention to remove any offsets, gain-errors, or higher order non-linearities in the circuits or the PMT. Depending on the actual gain characteristics of the particular type of PMT being used, a logarithmic amplifier, or an amplifier with some other non-linear transfer function, such as a power law (e.g., square root, cube root, etc.) may be substituted for amplifier 490 without altering the substance of the invention.

The gain signal 452 may then be subtracted from the PMT output or current signal 454 to result in output signal 488, which is then input to the gain adjustment module 451. The output signal (e.g., gain subtracted from measured signal 468) may also be input to defect (e.g., image) processor 412. Defect processor 412 may include mechanisms for processing the received data, such as buffering, compressing, packing, filtering noise, generating images based on the input signal, analyzing images to detect defects on the sample, etc. The majority of defects may be found by detecting contrast, defined as the ratio of the intensities in the target and reference dies, rather than by threshold, which is defined as the difference between the intensities. However, in conventional inspection systems, determining the ratio of the intensities is computationally expensive. By using a logarithmic representation, the difference of the log intensities may simply be obtained to get the log of the intensity ratio (e.g., via the processor 412). A threshold may then be applied to the log-ratio at a value that is equivalent to the desired threshold on the linear ratio to determine whether there is a defect.

Figure 5:
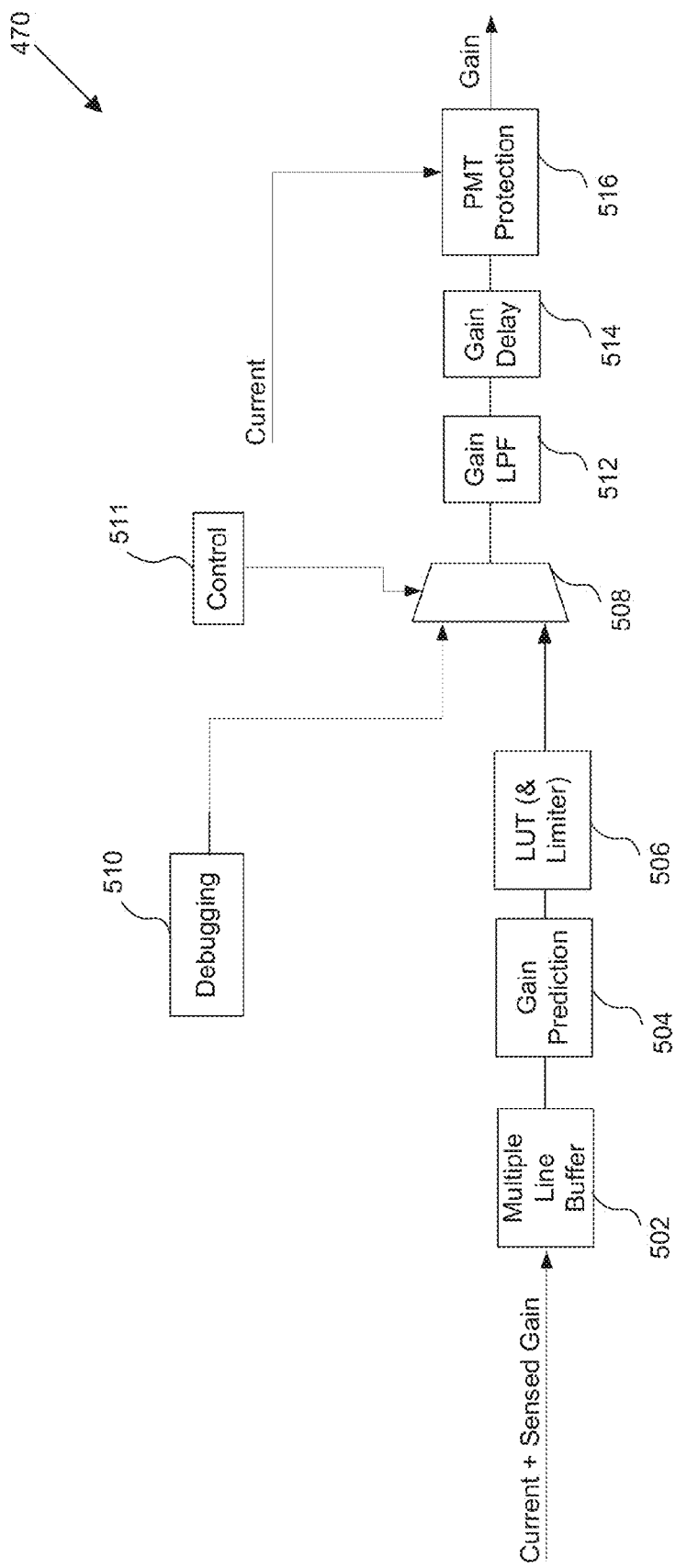
FIG. 5 is a diagrammatic representation of the gain prediction and adjustment module of FIG. 4 in accordance with a specific implementation of the present invention.

The gain adjustment portion may be implemented in any suitable manner. FIG. 5 is a diagrammatic representation of the gain prediction and adjustment module 470 of FIG. 4 in accordance with a specific implementation of the present invention. As shown in FIG. 5, the combined current response and gain signal (digitized output signal from PMT minus the digitized gain signal) may be received into a multiple line buffer 502. However, the buffer may be configured to hold a combined signal for only the single line that was last scanned. The buffer 502 may be configured to hold one or more lines that were last scanned immediately prior to the upcoming line that is to be scanned by the inspection tool.

The buffered one or more previous lines may then be received by a gain prediction module 504 that determines a gain value for the next scan line. This gain value may also be input to a look up table (LUT) 506, which is also a limiter, for ensuring that the gain value stays within acceptable values for other signal processing hardware components that further receive and/or process the gain, such as the digital to analog converter (DAC) 466. For example, LUT 506 is configured to ensure that the gain waveform is kept within minimum and maximum limits of the processing hardware. Hardware that may have particular gain limits includes the DAC 466. That is, the LUT 506 coverts the gain value into a form that the DAC 466 can read. For instance, a 12 bit DAC can only read values from 0 to 4096. For example, high gain values that the DAC 466 cannot produce may be converted by the LUT 506 to a maximum range of values that is readable by the DAC 466 so as to generate the highest analog gain range of values that can be output from the DAC 466.

The output of LUT 506 may also be input to a multiplexer 508, which also may be configured to receive other input for multiplying with output signal. In a specific implementation, the MUX 508 is arranged to receive a debugging signal from debugging module 510, which may be configured to debug the DAC 466 by repeatedly ramping up debugging input values. A control register 511 may be configured to control whether the MUX 508 outputs the debugging gain signal 510 or the predicted gain signal.

The gain signal may also be received by a gain LPF (low pass filter) 512 to limit the frequency of the gain signal to a particular frequency range, e.g., to 25 MHz or lower, for example, so as to minimize induction current. For instance, a high frequency gain signal may produce high induction current that causes unwanted artifacts in the system. Thus, a LPF 512 can be selected to limit the gain signal to be below a particular frequency maximum based on experimentation as to how high the frequency can go without producing unwanted artifacts.

The gain signal may also be received by a gain delay module 514 for aligning the output of the gain signal to coincide with the next line. For instance, the wiring and circuitry through which the gain signal travels may cause the gain signal to be output to the PMT too soon. Accordingly, the gain signal may be delayed based on when the next line is being scanned so that the gain for the next line is applied to the PMT when such next line is being scanned by the inspection tool. For instance, the gain for the first pixel of the next scan line is set to the gain that was predicted based on the first pixel of the previous scan line; the gain for the second pixel of the next scan line is set to the gain that was predicted based on the second pixel of the previous scan line; etc.

The gain signal, along with the detected response signal, may also be input to a PMT protection module 516 to ensure that the gain signal does not damage the PMT. For instance, if the detected light signal (e.g., detected PMT current) is too high, the gain signal may be clamped down to protect the PMT.

In one example implementation, the response for the next line may be predicted to be the same as the response of the previous one or more lines. If more than one line is used, the response from the multiple lines (e.g., 3 lines) may be averaged together to predict the response for the next line. The gain for the next line may then be set so as to keep the resulting response within a specified range of response values. In a specific example, the gain may be changed by about 3.5 orders of magnitude when the dynode voltages are modulated by about 25V (+/−12.5 V).

Figure 7:
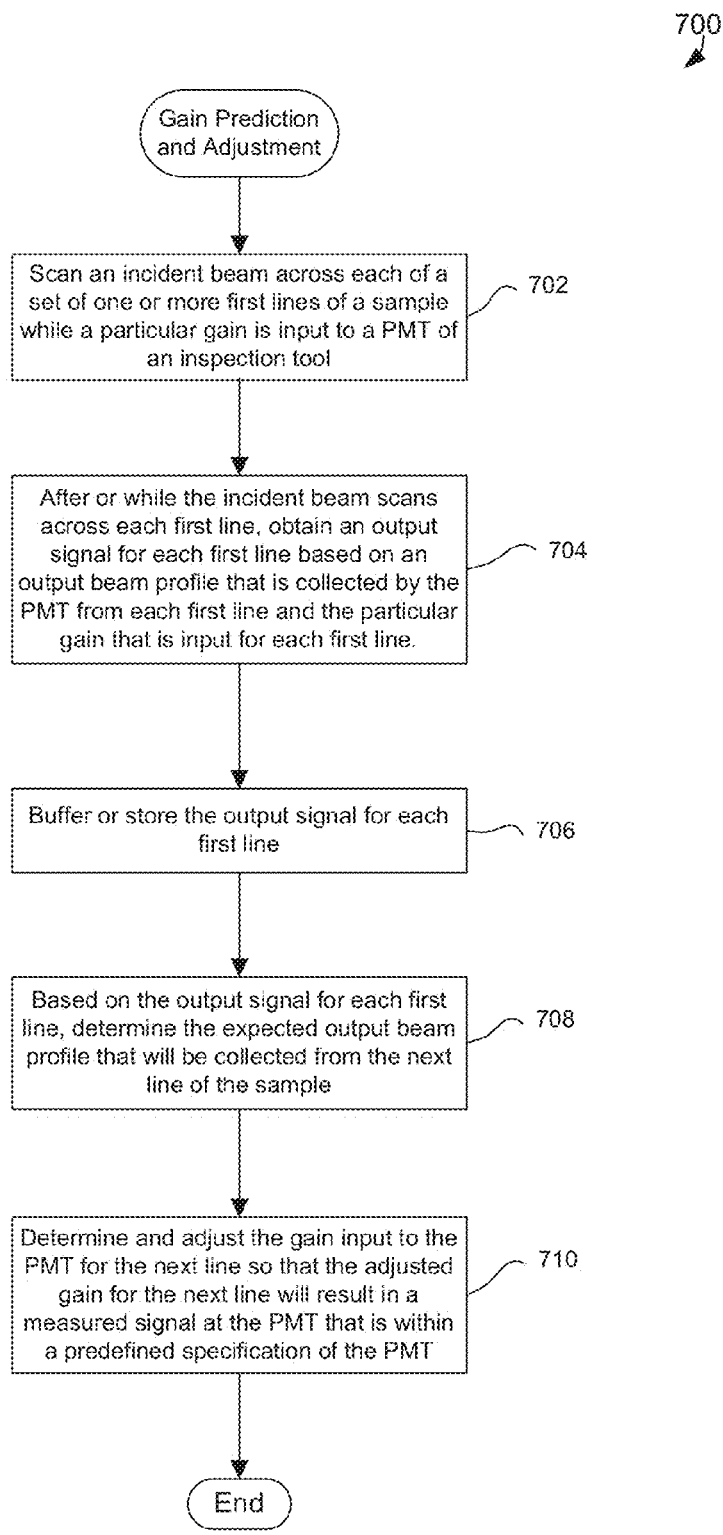
FIG. 7 is a flow chart illustrating a gain prediction and adjustment procedure in accordance with one embodiment of the present invention.

Gain for the next line can be predicted and set using any suitable technique or mechanism. FIG. 7 is a flow chart illustrating a gain prediction and adjustment procedure 700 in accordance with one embodiment of the present invention. Initially, an incident beam is scanned across each of a set of one or more first lines of a sample while a particular gain is input to a photomultiplier tube (PMT) of an inspection tool in operation 702. After or while the incident beam scans across each first line, an output signal is obtained for each first line based on an output beam profile collected by the PMT from each first line and the particular gain that is input for each first line in operation 704. For instance, as each first line is scanned with the incident beam, a sensor of the inspection tool collects light and converts such collected light into a measured signal and other components of the system then convert such measured signal into a digitized output signal (minus the particular gain) for such first line. The output signal for each first line may be buffered or stored for later use during gain prediction in operation 706.

Based on the output signal for the one or more first lines, the expected output beam profile that will be collected for the next line can then be determined in operation 708. For example, the expected output beam profile may be assumed to either be substantially equal to the output beam profile for the one or more first scan lines or to have a rate of gain increase or decrease that is substantially equal to a rate of gain increase or decrease for the one or more first scan lines. The expected output beam profile for the next line may then be used to determine and adjust the gain for the next line so that the adjusted gain will result in a measured signal at the PMT that is within a predefined specification of the PMT in operation 710. Although not shown, this process 700 is likely repeated for any number of lines (e.g. all or a substantial portion) of the sample.

The gain that is determined for each portion of the next line results in a gain waveform for the next line. The gain for each portion may be adjusted so that a predefined set point measured signal (e.g., anode current) of the sensor or PMT is maintained. There are tradeoffs for choosing a high set point vs. a low set point for the sensor. For example, if the set point is set too low, the amplifier that reads in the anode current (e.g., log amplifier 482) may be very slow. However, if the anode current is set too low, than the noise may get too high. Additionally, the gain for the next line may be adjusted to reduce the bandwidth so as to minimize artifacts as described herein. The gain may also be adjusted to account for limits of the hardware system, such as into a form that is readable by the DAC 466. The gain may also be delayed to account for propagation delays, e.g., of the DAC, cables, and the optical path.

In one implementation, the expected value of the light for the next scan is assumed to equal the measured value of light from the previous scan:

$$\text{Light}(x,y) = \text{Light}(x-1,y) \qquad \text{Equation [1]}$$

In Equation [1], the sample is being scanned relative to the beam in a y direction fast sweep, and then the sample moves relative to the beam in an x direction slow sweep. In other words, each scan line has a same x position. However, the surface of the sample may be scanned in any suitable direction. In general, a first portion of the sample is scanned, and then a second portion of the sample is scanned. The gain for the second portion can be predicted based on the light measures from the previously scanned first portion.

Various extrapolation based on multiple previous lines may also be employed. In a geometric linear extrapolation of the last two lines in log space the expected light for the next line is determined by the following:

$$\text{Light}(x,y) = \text{Light}(x-1,y) + (\text{Light}(x-1,y) - \text{Light}(x-2,y)) \quad \text{Equation [2]}$$

In this geometric linear extrapolation, the difference between the last two lines is added to the light value of the last line so as to capture increases from one line to another. For example, if the light is slowly increases, it may be assumed that the next line will also increase by a same amount as the increase between the last two lines.

In an alternative geometric partial linear extrapolation, the extrapolation may be biased such that the increase and decrease in light intensity is expected to be less (or more) than in the geometric linear extrapolation:

$$\text{Light}(x,y) = \text{LIght}(x-1,y) + \alpha(\text{Light}(x-1,y) - \text{Light}(x-2,y)) \quad \text{Equation [3]}$$

Equations [1] and [2] may be viewed as special cases of the geometric partial linear extrapolation of Equation [3] with $\alpha=0$ and 1, respectively. The weight a may be selected by determining how quickly the light intensity of the wafer changes from line to line. If the light intensity is slowly varying, a value closer to zero can be chosen. Conversely, if the wafer light intensity is quickly varying, a value closer to 1 may be used in order to catch up to the changing light intensity.

Figure 8A:
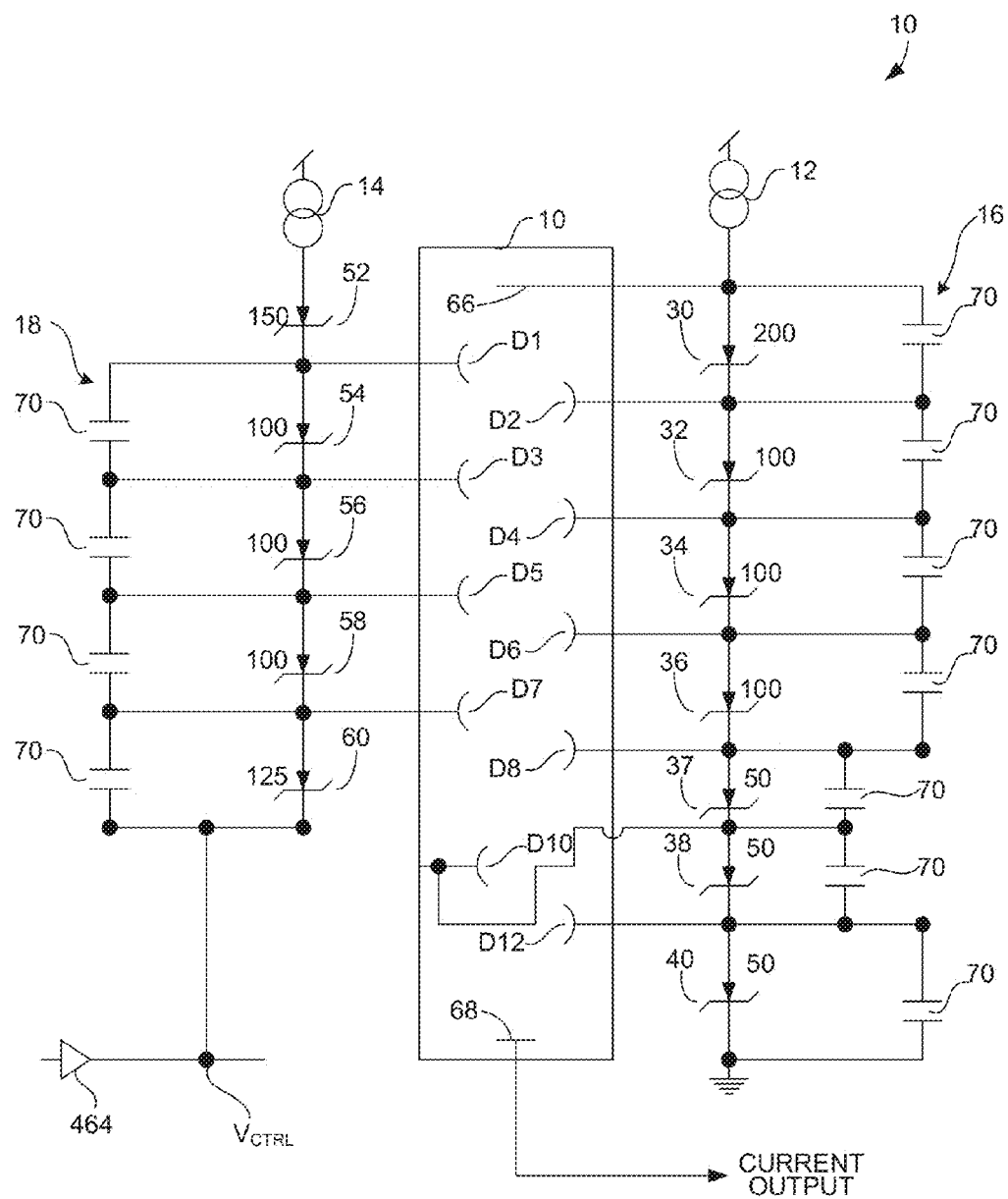
FIG. 8A is a schematic diagram illustrating a biasing circuit for a photomultiplier tube (PMT) according to a specific embodiment of the present invention.

FIG. 8A is a schematic diagram illustrating a biasing circuit for a photomultiplier tube (PMT) according to a specific embodiment of the present invention. As shown, a PMT 10, such as available from Hamamatsu Corporation of Hamamatsu City, Japan, furnished with ten dynodes, is depicted, although persons of ordinary skill in the art will appreciate that the invention could easily be adapted to PMT's from different manufacturers or having different numbers of dynodes.

In this illustrated embodiment, the PMT 10 is biased by two matched constant current sources 12 and 14 which drive two separate bias strings 16 and 18, one for a modulated and one for a fixed set of dynodes. The bias zener diode string 16 for even-numbered dynodes D2, D4, D6, D8, D10, and D12 includes series-connected zener diodes 30, 32, 34, 36, 37, 38, and 40 driven by constant current source 12, and is referenced to ground. These zener diodes may have voltage ratings, for example, of 200V, 100V, 100V, 100V, 50V, 50V and 50V, respectively.

The other bias zener diode string 18 for even-numbered dynodes D1, D3, D5 and 48 includes series connected zener diodes 52, 54, 56, 58 and 60, driven by constant current source 14. Bias zener diode string 18 may be referenced to a fast variable voltage source, Vctrl, at the output of amplifier 464. These zener diodes may have voltage ratings, for example, of 150V, 100V, 100V, 100V and 125V, respectively. Even though Vctrl may vary rapidly, the constant current sources driving the bias strings require only fixed DC voltages to operate.

The values of the zener diodes 30, 40, 52, and 60 may generally be chosen to offset the voltages at adjacent dynodes such that the voltage between adjacent dynodes decreases from the voltage at the cathode 66. Furthermore, when Vctrl is equal to 1.5 times the voltage on dynode D12, this voltage is called Vmax, the maximum gain control voltage.

Since the inter-dynode voltage within each of the two bias zener diode strings is constant, capacitors 70 may be placed in parallel with all the bias zener diodes, except zener diode 52, to lower the dynamic impedance of the bias strings. These capacitors can be made arbitrarily large, (e.g., 0.1 µF) without affecting the speed of the gain control circuit disclosed herein.

When Vctrl is equal to Vmax, the PMT 10 operates at its maximum gain. As Vctrl is made less negative, the inter-dynode voltages become alternately larger and smaller than their conventional values of a conventional biasing circuit. For example, as Vctrl is made less negative, the potential between dynodes D7 and D8 decreases while the potential between dynodes D7 and D6 increases. Therefore the gain at each dynode alternately increases or decreases. However, the gain decreases faster on the even dynodes than it increases on the odd dynodes. As a result, the overall PMT gain decreases.

As Vctrl approaches 0.5 times the voltage on dynode D12, the pairs of odd and even dynodes approach the same voltage and the overall tube gain is minimized. This voltage is called Vmin. As Vctrl approaches Vmin, the system becomes less accurate, due to component mismatches in the two bias strings. However, the circuit will still continue to attenuate the signal. This enables built in overload protection, with a fast recovery when the overload ends.

Figure 8B:
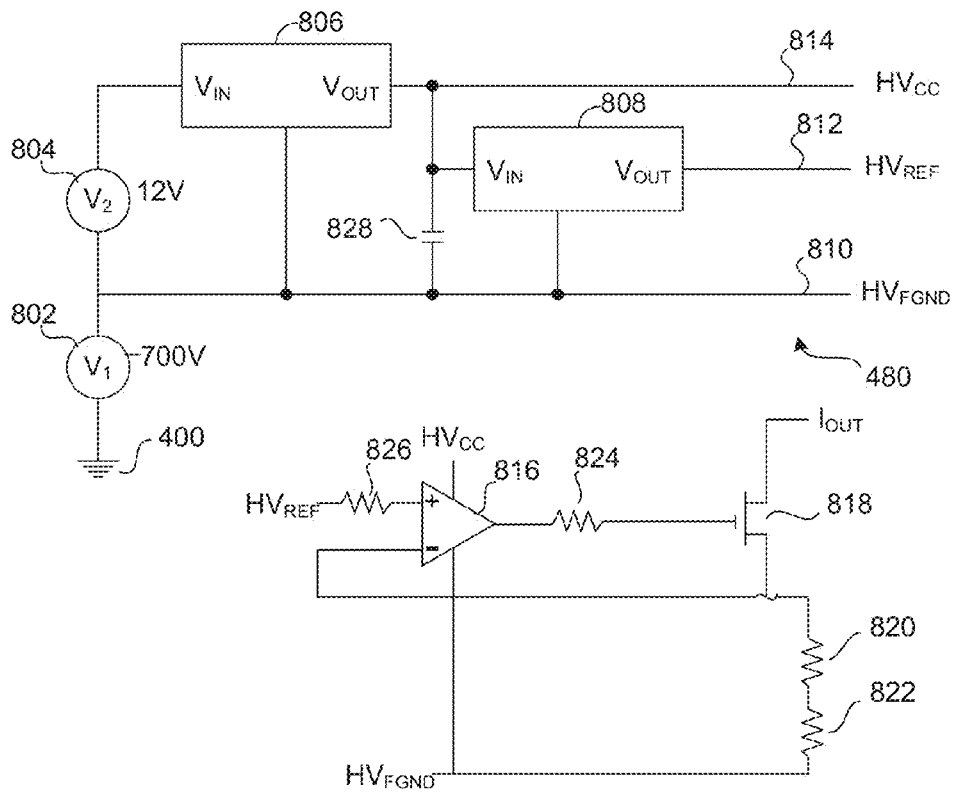
FIG. 8B is a schematic diagram illustrating the accurate matched current sources of FIG. 8A in accordance with one embodiment of the present invention.

The accurately matched current sources 12 and 14 of FIG. 8A for driving the two bias strings can each be implemented in any suitable manner. FIG. 8B illustrates a current source circuit using only two fixed voltage supplies, high voltage (HV) supply 802 and low-voltage (LV) supply 804. Unlike the supplies used with conventionally biased PMTs, the HV supply need not be particularly stable, because the current source acts as series regulator. High-voltage supply 802 may be a commercially-available high-voltage supply, such as a Model E06 available from EMCO High Voltage of Sutter Creek Calif., and low-voltage supply 802 may be a commercially-available 12V DC-DC converter with a high isolation voltage, such as a Model UWR-12/250-D12 available from DATEL of Mansfield Mass. Voltage regulator 806 may be a standard 3-terminal linear voltage regulator supplying a regulated voltage of 9 volts. Voltage regulator 808 may be a precision 3 terminal voltage reference providing a voltage reference of 4.096 volts. Lines 810, 812, and 814 are used to power the remainder of the circuit elements of FIG. 8B. High-voltage power supply 802 forms a high voltage "floating" ground, HVFGND at line 810, for the current sources. Low-voltage power supply 804 and voltage regulators 806 and 808 are referenced to this floating ground to generate the 4.096V reference voltage at line 812 and the 9 volt supply at line 814 used by the current source.

Amplifier 816 may be a moderate-speed, low offset, operational amplifier and MOS transistor 818 may be a high-voltage low capacitance N-channel MOSFET. Any suitable alternatives are available from numerous manufacturers, including Linear Technology, Analog Devices, Texas Instruments, Diodes Inc., etc.

Resistor 820 may take the form of a precision 3,000 ohm, 0.1% resistor (Panasonic) which is added to Resistor 822, an ordinary 1% 150 ohm resistor. In one embodiment, amplifier 816 adjusts the voltage at the gate of MOS transistor 818 to maintain a constant 4.096 volts across the 3,150 ohm combination of resistors 822 and 820 to HVFGND. This results in a precise 1.300 mA current flowing through MOS transistor 818. Since the gate of MOS transistor 818 is isolated, all the current must come from the load, at the drain of MOS transistor 818.

Resistors 824 and 826, and capacitor 828 are used, according to standard design practices, to correct for non-ideal behavior in the components. Resistor 824, which may have a value of about 50 ohms in the illustrated embodiment, isolates amplifier 816 from the gate capacitance of MOS transistor

818. Resistor 826, which may have a value of about 3,160 ohms in the embodiment shown, compensates for the input bias current of amplifier 816. Capacitor 828, which may have a value of about 1 µF in the embodiment shown, is a decoupling capacitor.

Figure 8C:
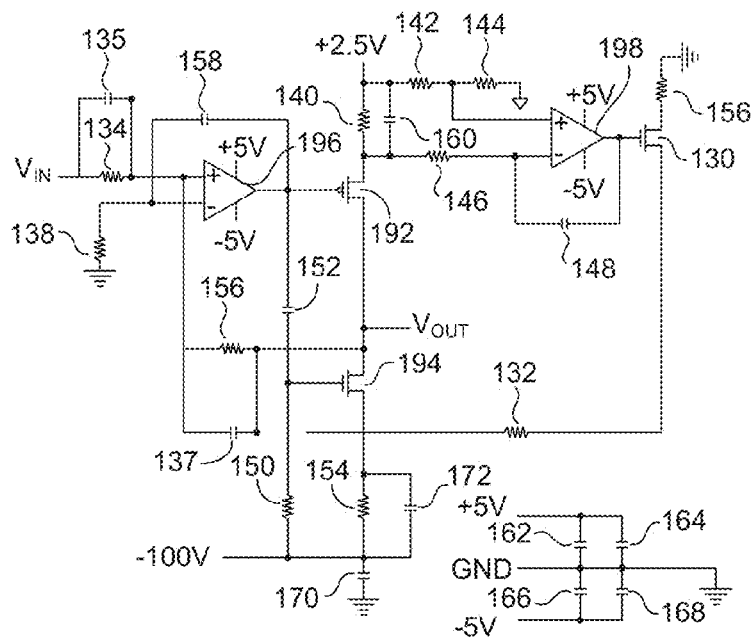
FIG. 8C is a schematic diagram showing one implementation of the amplifier circuit of FIGS. 4 and 8A.

In the illustrated embodiment, the high voltage amplifier 464 of FIG. 8A is a high-speed linear amplifier with a gain of about 35. FIG. 8C is a schematic diagram showing one implementation of the amplifier circuit 464 of FIGS. 4 and 8A. The amplifier circuit of FIG. 8C uses three power supplies and one voltage reference (not shown), having nominal output voltages of +5V, +2.50V, −5V and −100V, respectively. The output is driven by high voltage MOS transistors 192 and 194, which are wired in a high-gain, common-source configuration. To minimize drain capacitance, the normal operating range of the output is restricted to a range of about −25V to −75V. Amplifier 196 controls MOS transistor 192 directly, but only controls the high-frequency part of MOS transistor 194. The DC component of MOS transistor 194 is controlled by amplifier 198, through transistor 130 and resistor 132. Amplifier 198 actively adjusts the bias of MOS transistor 194 to maintain a constant source current on MOS transistor 192. By configuring the circuit so that the constant source current on transistor 192 is slightly larger than the largest possible current supplied to the load, it is ensured that transistor 194 is always slightly forward biased.

Restricting the operating range of the circuit of FIG. 8C and using active biasing ensures that neither MOS transistor 192 nor MOS transistor 194 is ever driven into saturation, or allowed to completely shut off This enables a very fast amplifier to be built.

Using an active biasing circuit minimizes power consumption by carefully tracking changes in the power supply voltages and automatically compensating for changes in the threshold voltages of any of the MOS transistors. If conventional biasing schemes were used, the system would have to be designed for the worst case combination of component values and supply voltages. This means that under normal operation the power consumption would be significantly higher.

Resistors 134 and 156 set the DC gain of the amplifier, while capacitors 135 and 137 may be selected to reduce the impedance of the feedback network while maintaining the same gain value at high frequencies. Resistor 138 compensates for input bias current in amplifier 196. Resistor 140 senses the DC bias current of MOS transistor 192. Resistors 142 and 144 set the reference voltage used to set the bias current of transistor 192. Resistor 146, together with capacitor 148, limits the bandwidth of the bias amplifier 198. Resistor 132 isolates the gate of MOS transistor 194 from the output capacitance of MOS transistor 130. Resistor 150 is a pull-up resistor to keep capacitor 152 charged. Resistors 154 and 156 limit the loop gain of bias amplifier 198 to prevent oscillations.

Capacitors 148 and 158, having values of 0.1 µF and 30 pF, respectively in the illustrated embodiment, are bandwidth limiting feedback capacitors, needed for stability. Capacitor 152, having a nominal value of 0.1 µF in the embodiment illustrated, is a DC blocking capacitor needed to allow amplifier 196 to control MOS transistor 194 even though it is outside the +/−5V operating range of amplifier 196. Capacitors 160, 162, 164, 166, 168, 170 and 172 are all bypass capacitors, and have nominal values of 0.1 µF in the embodiment illustrated.

In the illustrated embodiment of FIGS. 4, 5, and 8A-8C, a single gain input is utilized to control the PMT. In an alternative embodiment, two gain inputs are used to control the PMT.

Figure 9A:
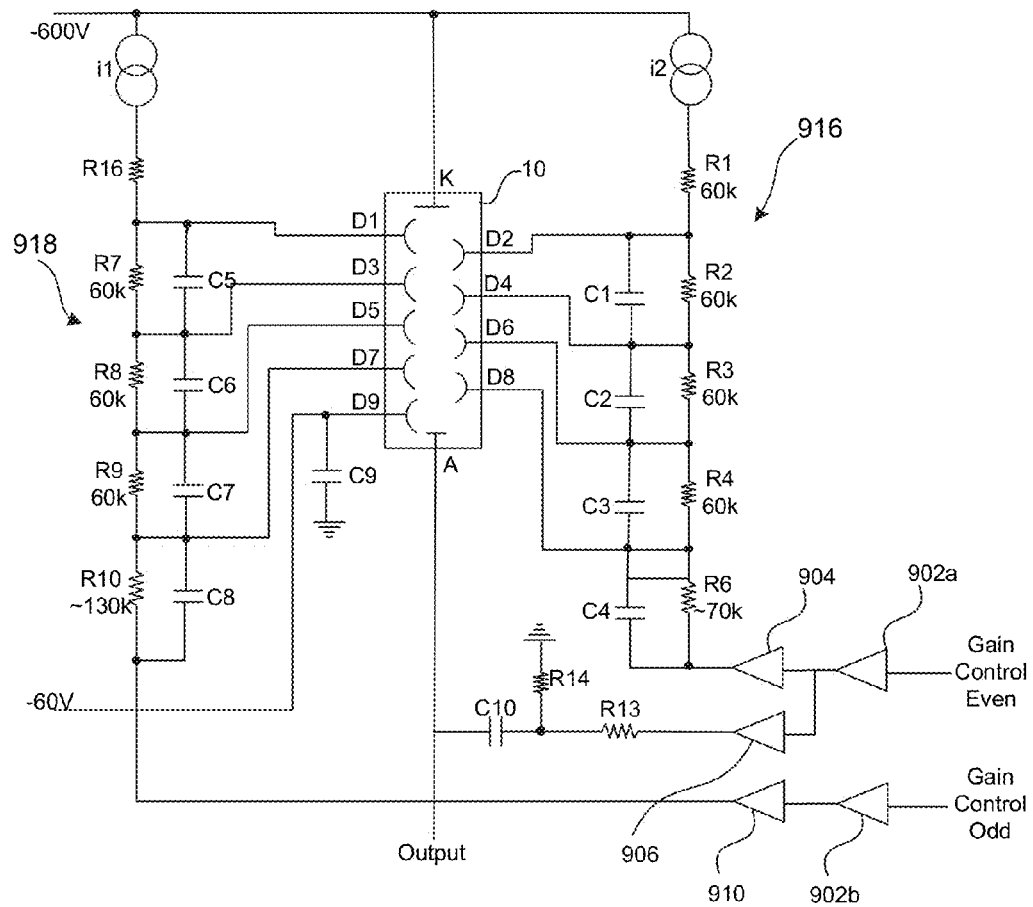
FIG. 9A is a schematic diagram illustrating the biasing circuit for a photomultiplier tube (PMT) having two gain inputs in accordance with an alternative embodiment of the present invention.

FIG. 9A is a schematic diagram illustrating the biasing circuit for a photomultiplier tube (PMT) having two gain inputs in accordance with an alternative embodiment of the present invention. As shown, the two inputs include a Gain Control Even signal input to amplifier 902*a* and a Gain Control Odd signal input to amplifier 902*b*. In a specific implementation, these two inputs may be used to modulate two sets of dynodes of the PMT 10 in opposite directions. As shown, one dynode set is the odd-numbered dynodes D1, D3, D5, D7, and the other dynode set is the even numbered dynodes D2, D4, D6, D8. The even-numbered dynodes are biased by even bias string 918 driven by constant current source i1, while the odd-numbered dynodes are biased by odd bias string 916 and driven by constant current source i2. As shown, bias string 918 is also referenced to ground. Any suitable current source, such as the current source circuit of FIG. 8B, may be used.

The amplifiers 902*a* and 902*b* are substantially matched and may have flat performance out to 35 MHz and minimal harmonic distortion. Measurements and numerical modeling show that optimal performance (PMT gain can be varied over 3.5 orders of magnitude; PMT bandwidth is independent of gain) may be achieved when the signal applied to Gain Control Even signal=(−1)×Gain Control Odd signal.

The values of the resistors and capacitors in each bias string may be selected so that the bias current is much larger than the electron multiplication current at each dynode. If this is not the case, the dynode voltages will change, which is undesirable for stable PMT performance. As shown, each of resistors R1-R4, R7 and R8 has a value of 60 kΩ, while each of capacitors C1-C8 has a value of about 0.001 uF. Capacitor C9 may have a value of about 1 uF The values of resistors R5 and R10 may be selected to provide optimal gain range and bandwidth. In one implementation, R5 is about 70 kΩ, and R10 is about 130 kΩ. Values for R13, R14, and C10 may be chosen to inject current into the anode circuit to compensate for current induced in the anode circuit by modulation of voltage on D1 through D8 driven by the Gain Control signals. For example, R13 has a value of 1 kΩ; R14 has a value of 1 GΩ; and C10 has a value of 0.2 pF.

One of the gain control amplifiers may be configured to directly drive the circuit that compensates for charge injection (e.g., capacitor C10 and resistors R13 and R14). Because the capacitive coupling between the odd dynodes and the anode may be larger than the coupling between the even dynodes and the anode, the circuit that compensates for charge injection is driven by the Gain Control Even signal. Fixed delays (e.g., Delays 904, 906, and 910) may also be inserted into the signal path to match arrival time at the anode to within about 1 nsec of current injected into the anode due to modulation of D2, D4, D6, and D8, current injected by the gain compensation circuit to within 1 nsec, and current injected into the anode by modulation of D1, D3, D5, and D7. For example, delay amplifiers 904, 906, and 910 may be configured to minimize the residual current injected into the anode A by the Gain Control signals when the Gain Control Even signal is 180 degrees out of phase with the Gain Control Odd signal.

The PMT gain control may be adjusted in two phases to null out any injected anode current associated with gain modulation to below 0.1 uA. Two 25 MHz signals with a phase difference of 180 degrees may be injected into the Gain Control Odd and Gain Control Even signal paths, respectively, with amplitude sufficient to modulate gain over a range of substantially 3 orders of magnitude. An adjustable value of resistor R14 may be iteratively adjusted and, accordingly, the phase difference between the Gain Control Odd and Gain Control Even signal iteratively adjusted until the Gain Control signals are about 180 degrees out of phase. This adjustment to R14 can be made at the time of manufacture of the PMT control board.

Figure 9B:
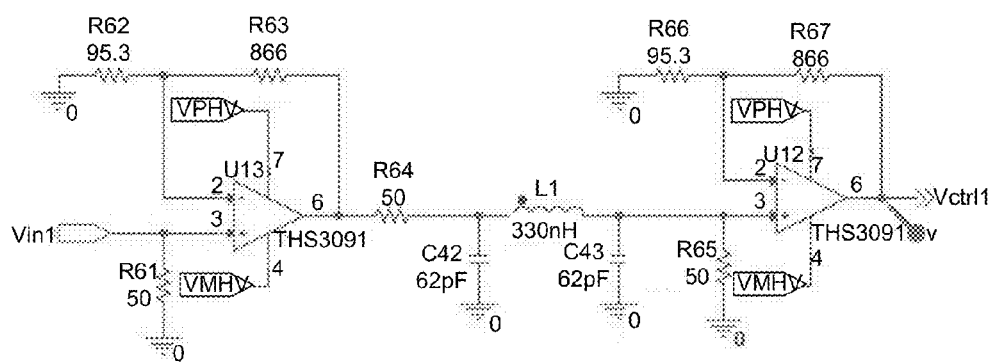
FIG. 9B is a schematic diagram showing one implementation of the two gain amplifier circuits of FIG. 9A.

FIG. 9B is a schematic diagram showing one implementation of the two gain amplifier circuits 902a and 902b of FIG. 9A. As shown, an input signal Vin1 is input to amplifier U13. Exemplary values for resistors R62-R67, capacitors C42 and C43, and inductor L1 are shown in FIG. 9B. In this embodiment, resistors R62 and R63 may provide current control in the feedback path of such amplifier U13. An intermediate arrangement of resistors R64 and R65, capacitors C42 and C43, and inductor L1 provide a low pass filter between the first amplifier U13 and a second amplifier U12. Resistors R66 and R67 set the gain of amplifier U12, which outputs the final Gain Control signal (even or odd). Voltage supplies VPHV and VMHV are each provided to the two amplifiers U12 and U13 and may be set to values of +/−15V. Example components that may be used as amplifiers U12 and U13 are THS3091 available from Texas Instruments of Dallas, Tex.

Figure 10:
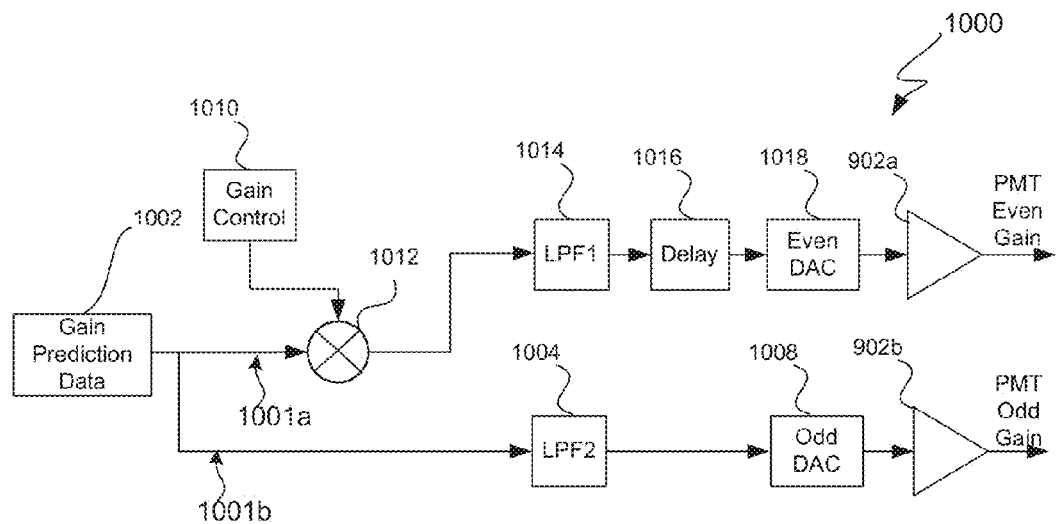
FIG. 10 is a schematic diagram illustrating a high-speed logarithmic photo-detector system for outputting two PMT gain signals in accordance with a second embodiment of the present invention.

FIG. 10 is a schematic diagram illustrating a high-speed logarithmic photo-detector system 1000 for outputting two PMT gain signals in accordance with a second embodiment of the present invention. As shown, the detector system 1000 receives gain prediction data 1002 into both an even signal path 1001a for outputting a PMT Even Gain signal and an odd signal path 1001b for outputting a PMT Odd Gain signal. Gain prediction data 1002 may include the gain that was predicted based on detected signals from a previous scan line and is to be used for a next scan line. The predicted gain may be determined as described above.

In the even path 1001a, a multiplier 1012 is arranged to receive, amplify (or reduce), and invert gain prediction data 1002 based on a Gain Control signal 1010. The multiplier 1012 may be arranged to slightly amplify the gain prediction data 1002 based on Gain Control signal 1010 so as to facilitate nullifying the injected anode current due to gain modulation.

Prior to outputting the PMT Odd and Even Gain signals, the gain prediction signals are both received into a low pass filter (LPF1 and LPF2) so as to minimize induction currents in the PMT. The gain prediction algorithm may predict a gain that changes very quickly. However, if the gain is adjusted too quickly, large induction currents may be induced in the PMT, resulting in artifacts in the detected PMT signal.

After a low pass filtering is performed, the odd dynode gain prediction signal may be input directly to odd DAC 1008 and then out to the odd dynodes via amplifier 902b. In contrast, the even gain signal may be slightly adjusted to minimize induction currents. The coupling between the even dynodes and the anode tends to be slightly different, as compared to the odd dynodes and the anode. If both sets of dynodes received the same signal (with just one inverted compared to the other), the induction current on the anode from both sets of dynodes would not cancel out exactly (the induction current is proportional to the coupling). The Gain Control signal input to the multiplier 1012 may be selected to either make the even dynode signal larger or smaller and a delay module 1016 may be configured to shift the even dynode signal slightly in time such that the induction current of the two sets of dynodes will exactly cancel out. If the coupling for both the even and odd dynodes were equal, the same (with one inverted) signal may be sent to each set of dynodes and the gain control signal 1010 and delay module 1016 could be eliminated.

LPF1 and LPF2 may be implemented in any suitable manner (e.g., in firmware) so as to compensate for non-ideality of the Gain Control Amplifiers 902a and 902b. Periodically during operation, (e.g., every 20 minutes), Gain Control signal 1010 and Delay module 1016 may be recalibrated to null the injected anode current due to gain modulation. Preferably, gain matching is maintained to about 0.1% and the delay adjustment is set with a resolution of about 20 psec. This recalibration may take a few milliseconds and be run when the PMT is idle. In sum, this recalibration may be configured to correct for drifts in PMT dynode capacitance difference over time and drifts in gain of the PMT Gain Control Amplifiers 902a and 902b and the time delay of PMT dynodes.

Figure 11:
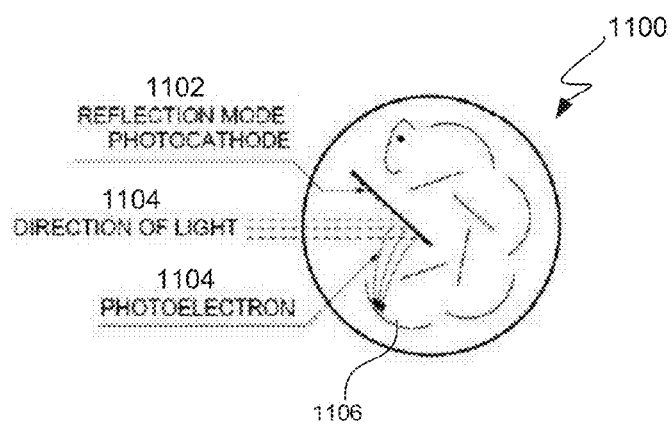
FIG. 11 is a diagrammatic representation of a circular cage type PMT.

Any suitable type of PMT may be utilized. By way of examples, the basic approach can also be applied to various types of PMT geometries, such as "Linear Focused" geometries or circular cage geometries. FIG. 11 is a diagrammatic representation of a circular cage type PMT 1100. In this simple example of PMT operation, detected light received in direction 1104 may reflect off reflection mode photocathode 1102 so that photoelectrons are received by dynode 1106.

For a production PMT, the arrangement of the Cathode, Dynodes and Anode may be designed to maximize the PMT bandwidth under the standard operating conditions as specified by the manufacturer. In certain embodiments of the invention, the PMT is operated so that PMT bandwidth remains high as PMT gain is reduced.

In a conventionally biased PMT, electrons generally start at the cathode, and then most electrons are finally collected at the anode. However, when the dynodes of the PMT are modulated as described above, the electron traces change dramatically so that more and more electrons miss the face of the dynodes and hence, terminate prior to reaching the anode, which works to lower the gain of the PMT.

Figure 12:
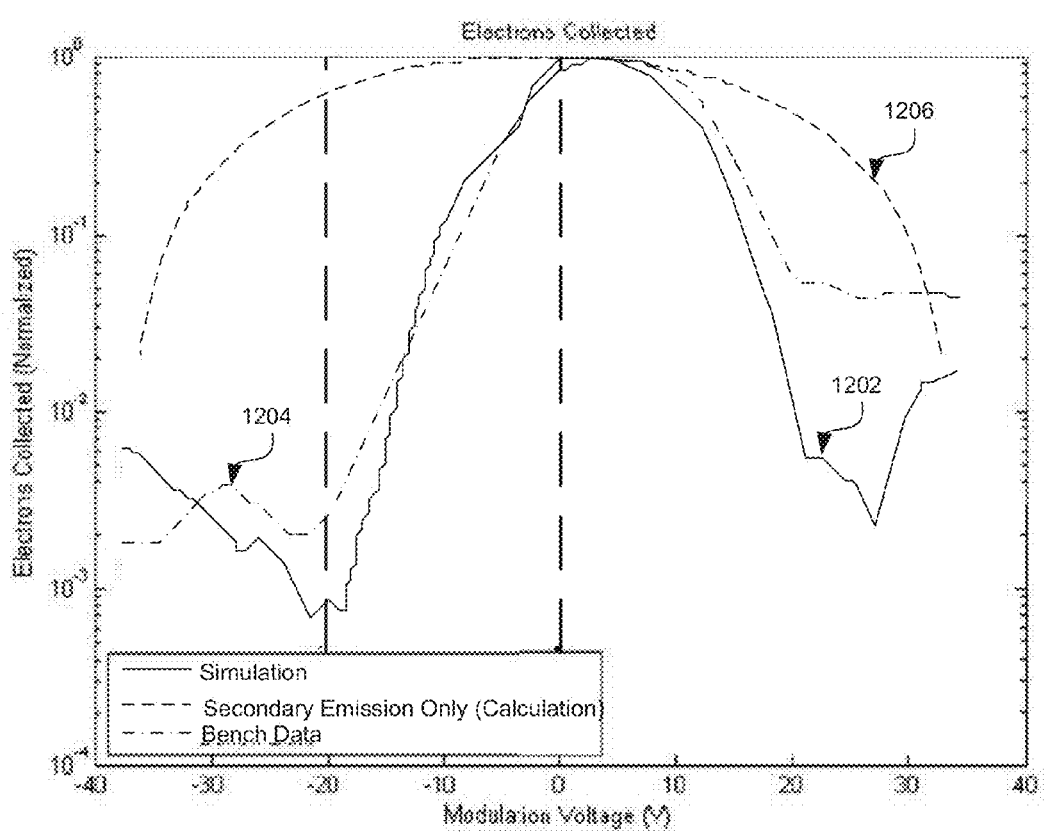
FIG. 12 illustrates the ratio of electrons collected at the anode to the maximum number of electrons collected (the gain) plotted versus modulation voltage.

FIG. 12 illustrates the ratio of electrons collected at the anode to the maximum number of electrons collected the gain) plotted versus modulation voltage. The dashed vertical black lines denote the region of interest for dynode modulation since this region contains the largest change in gain for the smallest voltage modulation. As shown, the solid curve 1202 is obtained based on electron optics simulations; the dash-dot-dash curve 1204 is obtained from bench data; and the dashed curve 1106 is obtained by calculating gain, assuming that there is no loss of gain from electrons missing dynodes (only using secondary emission principles as described in U.S. Pat. No. 6,177,665). As can be seen, most of the gain reduction is due to the electrons missing dynodes (curve 1202), not from the change in secondary emission characteristics due to the change in dynode voltages (curve 1106, which is on mechanism of gain change described in patent U.S. Pat. No. 6,177,665).

Figure 13:
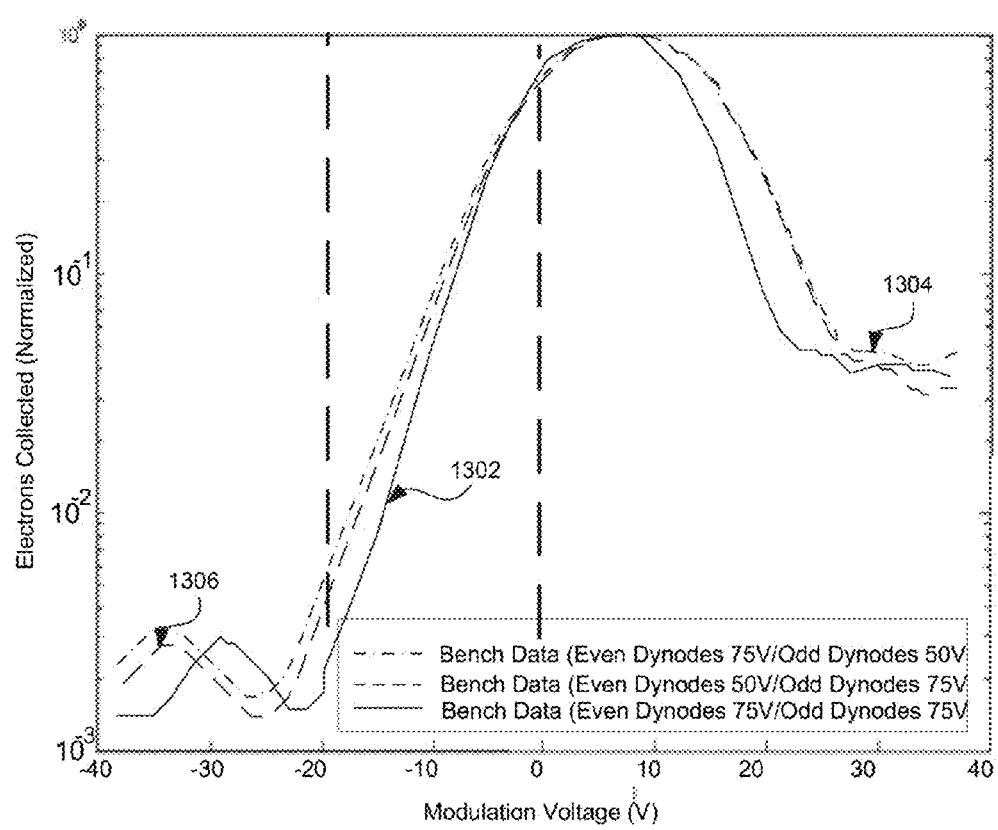
FIG. 13 illustrates different bench gain data for different dynode modulation schemes.

The above-described data pertains to symmetric dynode modulation (the odd and even dynodes move in equal amounts in opposite directions). Data was also obtained during testing (bench data) for asymmetric cases, which could be used in order to minimize anode induction currents. FIG. 13 illustrates different bench data (Gain) for different dynode modulation schemes. The solid curve 1302 shows symmetric dynode modulation; the dash-dot-dash curve 1304 corresponds to even dynodes being modulated more than the odd dynodes, while the dashed curve 1306 corresponds to the odd dynodes being modulated more than the even dynodes. The symmetric case appears to give the best performance (maximum gain change with minimum dynode modulation), but the other two cases are also acceptable, though not ideal. Again, the dashed vertical lines denote the region of interest for dynode modulation.

Bandwidth data was also obtained for different modulation schemes (not shown). The resulting data appears to indicate that the symmetric case is the best choice while the other two asymmetric cases are still acceptable.

Certain embodiments may facilitate a reduced voltage swing of the control amplifier by 2x, which can then allow doubling of the maximum slew-rate of the in the PMT gain. Additionally, the voltage swing of the control amplifier being reduced by about 2x also can enable a substantial reduction of harmonic distortion so there can be more accurate cancellation of the current injected into the anode by the parasitic capacitances to the dynodes that control the gain. It is significantly easier to design gain modulation amplifiers with low harmonic distortion. Power dissipation in the output transistors can also be reduced by about 4x, which will increase reliability. These comparisons are relative to implementation of the invention described in U.S. Pat. No. 6,177,665.

With the certain design embodiments, the net current injected into the anode by gain modulation can be below 0.5 µA, which is close to the target noise floor for the anode current amplifier. In contrast, other gain control designs can result in the net injected current being over 20 uA, which is far above the anode current noise floor. This large net injected current has a complex dependence on the history of the prior history of the anode current, and it would be impractical to use firmware to numerically remove this effect from the signal. Also, sensitivity to defects in regions of rapid gain change would be poor in other gain designs.

The inspection techniques described herein may be implemented on various specially configured inspection or metrology systems, such as the one schematically illustrated in FIG. 1. In certain embodiments, a system for inspecting or measuring a specimen includes at least one memory and at least one processor that are configured to perform the techniques described herein. The memory and/or processor may be implemented by any suitable combination of hardware and/or software, such as a programmable device or field programmable gate array (FPGA). The signals captured by the detector (e.g., PMT) can be processed by a computer system or, more generally, by a signal processing device. The computer system may be configured (e.g., with programming instructions) to provide a user interface (e.g., on a computer screen) for displaying resultant inspection characteristics. The computer system may also include one or more input devices (e.g., a keyboard, mouse, joystick) for providing user input, such as changing detection parameters. In certain embodiments, the computer system is configured to carry out inspection techniques detailed herein. The computer system typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting or measuring a specimen, the method comprising:
    directing an incident beam across a plurality of consecutive scan lines of a specimen so that an output beam profile from each scan line is consecutively collected by a photomultiplier tube (PMT), wherein the scan lines include one or more first scan lines and a next scan line that is scanned after the one or more first scan lines;
    after or while the incident beam is directed to the one or more first scan lines of the specimen and prior to the incident beam being directed to the next scan line, receiving data for the one or more output beam profiles for the one or more first scan lines from the PMT into a line buffer for holding data for the entire one or more first scan lines;
    prior to the incident beam being directed to the next scan line, determining an expected output beam profile for the next scan line based on data for the one or more output beam profiles that are received into the line buffer for the one or more first scan lines, wherein the expected output beam profile is determined to have a substantially same value or a same rate of gain increase or decrease as the one or more output beam profiles for the one or more first scan lines; and
    as the incident beam is directed towards the next scan line, setting a gain input to the PMT for the next scan line based on the expected output beam profile so that the gain for such next scan line results in a measured signal at the PMT that is within a predefined specification of the PMT or other hardware components that receive a measured signal from the PMT.

2. The method of claim 1, wherein each one or more first scanned lines are on a first die and the next scan line is on a second die that differs from each one or more first die.

3. The method of claim 1, wherein each one or more first scanned lines comprises a plurality of first scan lines and the next scan line is adjacent to the first scan lines.

4. The method of claim 1, further comprising analyzing data for the one or more output beam profiles for the one or more first scan lines to detect defects in such one or more first scan lines.

5. The method of claim 1, wherein the scan lines, towards which the incident beam is directed, further include a second next scan line that is adjacent to the first next scan line, wherein the method further comprises:
    after or while the incident beam is directed to the first next scan line of the specimen, receiving data for an output profile for the first next scan line from the PMT into the line buffer;
    determining an expected output beam profile for the second next scan line based on the data for the output beam profile that is received into the line buffer for the first next scan line; and
    as the incident beam is directed towards the second next scan line, setting a gain input to the PMT for the second next scan line based on the expected output beam profile for the second next scan line so that the gain for such second next scan line results in a measured signal at the PMT that is within a predefined specification of the PMT.

6. The method of claim 5, wherein the gain input to the PMT for the first and second next scan line are set so as to be limited to a particular frequency range.

7. The method of claim 1, wherein the expected output beam profile for the next scan line is predicted to be substantially equal to the output beam profile for a most recently scanned one of the first scan lines or an average of the output beam profiles for the one or more first scan lines.

8. The method of claim 1, wherein the gain input is in the form of a gain control waveform and the one or more first scan lines comprise a plurality of first scan lines and the expected output beam profile for the next scan line is predicted to have a rate of gain increase or decrease from the immediately previously scanned one of the first scan lines that is substantially equal to a rate of gain increase or decrease for first scan lines.

9. The method of claim 1, wherein the one or more first scan lines comprise a plurality of first scan lines and the expected output beam profile is predicted to have a rate of gain increase or decrease from the immediately previously scanned one of the first scan lines that is proportional to a rate of gain increase or decrease for the first scan lines.

10. The method of claim 1, wherein the gain is further set so that such gain is aligned to coincide with scanning of the next scan line and kept within a predetermined range of values so as to minimize artifacts in an image generated from a measured signal output by the PMT for the next scan line.

11. The method of claim 1, wherein the gain is input to the PMT for the next scan line by inputting two gain signals to the PMT that are 180 degrees out of phase and substantially identical in magnitude, wherein one of the two gain signals is received by a first half of dynodes of the PMT and another one of the two gain signals is received by another half of dynodes of the PMT.

12. An system for inspecting or measuring a specimen, comprising:
   a photomultiplier tube (PMT) for sensing light emanating from a specimen in response to an incident beam directed towards such specimen;
   a beam generator for directing the incident beam across a plurality of consecutive scan lines of the specimen so that an output beam profile from each scan line is consecutively collected by the PMT, wherein the scan lines include one or more first scan lines and a next scan line that is scanned after the one or more first scan lines;
   a detection module including the PMT and one or more detection components for generating a response signal for each scan line as the incident beam is scanned over such scan lines; and
   a gain prediction module including a line buffer for receiving data for the response signal for each scan line from the detection module and setting a gain of the PMT based on such response signal, wherein the gain for each scan line of the specimen is set based on predicting the light that is expected to emanate from such scan line based on data for the response signal received for all of the one or more previous scan lines of the specimen that were most recently scanned by the incident beam and prior to such scan line being scanned by the incitement beam.

13. The system of claim 12, wherein the gain input for each scan line is in the form of a gain control waveform for such scan line that results in a measured signal at the PMT that is within a predefined specification of the PMT or other hardware components of the detection module or gain prediction module that receive a measured signal from the PMT.

14. The system of claim 12, further comprising a processor for analyzing the response signal for each scan line to detect defects in such scan line.

15. The system of claim 12, wherein the gain input to the PMT for each scan line is set so as to be limited to a particular frequency range.

16. The system of claim 12, wherein the light from each scan line is predicted to be substantially equal to the light from the one or more previous scan lines, which is determined from the response signal from such one or more previous scan lines.

17. The system of claim 12, wherein the one or more previous scan lines comprise a plurality of previous scan lines and the light from each scan line is predicted to have a rate of gain increase or decrease from the immediately previously scanned one of the previous scan lines that is substantially equal to a rate of gain increase or decrease for the previous scan lines.

18. The system of claim 12, wherein the one or more previous scan lines comprise a plurality of previous scan lines and the light from each scan line is predicted to have a rate of gain increase or decrease from the immediately previously scanned one of the previous scan lines that is that is proportional to a rate of gain increase or decrease for the previous scan lines.

19. The system of claim 12, wherein the gain input for each scan line is further set so that such gain input is aligned to coincide with scanning of such scan line and kept within a predetermined range of values so as to minimize artifacts in an image generated from a measured signal output by the PMT for such scan line.

20. The system of claim 12, wherein the gain input to the PMT for each scan line is accomplished by inputting two gain signals to the PMT that are 180 degrees out of phase and substantially identical in magnitude, wherein one of the two gain signals is received by a first half of dynodes of the PMT and another one of the two gain signals is received by another half of dynodes of the PMT.

21. At least one computer readable storage medium having computer program instructions stored thereon that are arranged to cause an inspection or metrology tool to perform the following operations:
   directing an incident beam across a plurality of consecutive scan lines of a specimen so that an output beam profile from each scan line is consecutively collected by a photomultiplier tube (PMT), wherein the scan lines include one or more first scan lines and a next scan line that is scanned after the one or more first scan lines;
   after or while the incident beam is directed to the one or more first scan lines of the specimen and prior to the incident beam being directed to the next scan line, receiving data for the one or more output beam profiles for the one or more first scan lines from the PMT into a line buffer for holding data for the entire one or more first scan lines;
   prior to the incident beam being directed to the next scan line, determining an expected output beam profile for the next scan line based on data for the one or more output beam profiles that are received into the line buffer for the one or more first scan lines, wherein the expected output beam profile is determined to have a substantially same value or a same rate of gain increase or decrease as the one or more output beam profiles for the one or more first scan lines; and
   as the incident beam is directed towards the next scan line, setting a gain input to the PMT for the next scan line based on the expected output beam profile so that the gain for such next scan line results in a measured signal at the PMT that is within a predefined specification of the PMT or other hardware components that receive a measured signal from the PMT.

22. The at least one computer readable storage medium of claim 21, wherein the gain input to the PMT for each scan line is accomplished by inputting two gain signals to the PMT that are 180 degrees out of phase and substantially identical in magnitude, wherein one of the two gain signals is received by a first half of dynodes of the PMT and another one of the two gain signals is received by another half of dynodes of the PMT.

* * * * *